United States Patent
Trumm et al.

(10) Patent No.: US 11,561,413 B2
(45) Date of Patent: Jan. 24, 2023

(54) POPULATION OF AN EYE MODEL USING MEASUREMENT DATA IN ORDER TO OPTIMIZE SPECTACLE LENSES

(71) Applicant: Rodenstock GmbH, Munich (DE)

(72) Inventors: Stephan Trumm, Munich (DE); Wolfgang Becken, Neuried (DE); Helmut Altheimer, Baisweil-Lauchdorf (DE); Adam Muschielok, Munich (DE); Yohann Bénard, Munich (DE); Gregor Esser, Munich (DE); Werner Mueller, Oetisheim (DE)

(73) Assignee: Rodenstock GmbH, Munich (DE)

( * ) Notice: Subject to any disclaimer, the term of this patent is extended or adjusted under 35 U.S.C. 154(b) by 322 days.

(21) Appl. No.: 16/479,122

(22) PCT Filed: Jan. 24, 2018

(86) PCT No.: PCT/EP2018/051715
§ 371 (c)(1),
(2) Date: Sep. 19, 2019

(87) PCT Pub. No.: WO2018/138140
PCT Pub. Date: Aug. 2, 2018

(65) Prior Publication Data
US 2020/0285071 A1    Sep. 10, 2020

(30) Foreign Application Priority Data

Jan. 27, 2017  (DE) .......................... 102017000772.1
Aug. 23, 2017  (DE) .......................... 102017007975.7
Aug. 23, 2017  (DE) .......................... 102017007990.0

(51) Int. Cl.
*G02C 7/02*    (2006.01)
*A61B 3/00*    (2006.01)
(Continued)

(52) U.S. Cl.
CPC ............ *G02C 7/027* (2013.01); *A61B 3/0025* (2013.01); *A61B 3/1005* (2013.01); *A61B 3/107* (2013.01);
(Continued)

(58) Field of Classification Search
CPC ........ G02C 7/024; G02C 7/027; G02C 7/028; A61B 3/0025; A61B 3/1005;
(Continued)

(56) References Cited

U.S. PATENT DOCUMENTS 7,931,374 B2    4/2011  Dai et al.
8,998,415 B2    4/2015  Norrby et al.
(Continued)

FOREIGN PATENT DOCUMENTS

DE         10313275 A1    10/2004
DE      102007032564 A1     1/2009
(Continued)

OTHER PUBLICATIONS

PCT International Search Report issued for PCT/EP2013/000073, dated May 6, 2013.
(Continued)

*Primary Examiner* — Jordan M Schwartz
(74) *Attorney, Agent, or Firm* — Banner & Witcoff Ltd.

(57) ABSTRACT

A method, a device, and a corresponding computer program product for calculating (optimizing) and producing a spectacle lens with the aid of a semi-personalized eye model. In one approach, the method includes providing personalized refraction data of at least one eye of the spectacles wearer; establishing a personalized eye model in which at least the parameters: shape of an anterior corneal surface of a model eye; a cornea-lens distance; parameters of the lens of the model eye; and lens-retina distance are established using personalized measured values for the eye of the spectacles (Continued)

wearer, and/or using standard values, and/or using the provided personalized refraction data, such that the model eye has the provided personalized refraction data, wherein at least the establishment of the lens-retina distance takes place via calculation.

22 Claims, 1 Drawing Sheet

(51) Int. Cl.
    *A61B 3/10*     (2006.01)
    *A61B 3/117*     (2006.01)
    *G16H 50/50*     (2018.01)
    *A61B 3/107*     (2006.01)

(52) U.S. Cl.
    CPC ............ *A61B 3/117* (2013.01); *A61B 3/1173* (2013.01); *G02C 7/028* (2013.01); *G16H 50/50* (2018.01)

(58) Field of Classification Search
    CPC ....... A61B 3/1015; A61B 3/102; A61B 3/107; A61B 3/117; A61B 3/1173
    See application file for complete search history.

(56) References Cited

U.S. PATENT DOCUMENTS

| | | | |
|---|---|---|---|
| 9,636,214 B2 | 5/2017 | Piers et al. | |
| 9,696,563 B2 | 7/2017 | Trumm et al. | |
| 2002/0085172 A1 | 7/2002 | Altmann | |
| 2003/0107706 A1 | 6/2003 | Rubinstein et al. | |
| 2004/0257527 A1 | 12/2004 | Qi et al. | |
| 2007/0002274 A1 | 1/2007 | Somani et al. | |
| 2008/0221674 A1 | 9/2008 | Blum et al. | |
| 2010/0145489 A1 | 6/2010 | Esser et al. | |
| 2010/0198515 A1 | 8/2010 | Becken et al. | |
| 2011/0228225 A1 | 9/2011 | Liang | |
| 2011/0299032 A1 | 12/2011 | Becken et al. | |
| 2012/0008090 A1 | 1/2012 | Atheimer et al. | |
| 2012/0033179 A1 | 2/2012 | Kratzer et al. | |
| 2012/0188504 A1 | 7/2012 | Petignaud et al. | |
| 2013/0035760 A1 | 2/2013 | Portney | |
| 2013/0100409 A1 | 4/2013 | Grant et al. | |
| 2014/0333897 A1* | 11/2014 | Becken .................. | A61B 3/103 351/211 |
| 2015/0002810 A1* | 1/2015 | Altheimer .............. | G02C 7/027 351/159.76 |
| 2015/0131054 A1* | 5/2015 | Wuellner ............. | A61B 3/0025 351/211 |
| 2015/0309338 A1 | 10/2015 | Chauveau et al. | |
| 2018/0092524 A1* | 4/2018 | Ng .......................... | G09B 23/30 |
| 2018/0344157 A1* | 12/2018 | Ng .......................... | A61B 3/145 |
| 2020/0218087 A1* | 7/2020 | Grand-Clement ... | G02C 13/005 |
| 2020/0221947 A1* | 7/2020 | Mino ....................... | G06T 7/11 |

FOREIGN PATENT DOCUMENTS

| | | |
|---|---|---|
| DE | 102012000390 A1 | 7/2013 |
| JP | 2008-542831 A | 11/2008 |
| JP | 2010-517089 A | 5/2010 |
| JP | 2010-221050 A | 10/2010 |
| WO | 02/084381 A2 | 10/2002 |
| WO | 02/088830 A1 | 11/2002 |
| WO | WO-2008/089999 A1 | 7/2008 |
| WO | WO-2010/084019 A1 | 7/2010 |
| WO | WO-2010/124991 A1 | 11/2010 |
| WO | WO-2013/104548 A1 | 7/2013 |

OTHER PUBLICATIONS

Office Action dated Oct. 7, 2015 for Japanese Patent Application No. 2014-551573 (with English translation).
Salmon, et al., "Normal-Eye Zernike Coefficients and Root-Mean-Square Wavefront Errors", Journal of Cataract & Refractive Surgery, vol. 32, issue 12, pp. 2064-2074, 2006.
Porter, et al., "Monochromatic Aberrations of the Human Eye in a Large Population", Journal of the Optical Society of America A, vol. 18, issue 8, pp. 1796-1803, 2001.
Esser, et al., "Derivation of the Refraction Equations for Higher Order Aberrations of Local Wavefronts at Oblique Incidence", Journal of the Optical Society of America A, vol. 27, issue 2, pp. 218-237, 2010.
Esser, et al., "Derivation of the Propogation Equations for Higher Order Aberrations of Local Wavefronts", Journal of the Optical Society of America A, vol. 28, issue 12, pp. 2442-2458, 2011.
Rabbetts, R. B., "Bennett & Rabbetts' Clinical Visual Optics", Butterwort Heinemann Elsevier Health Sciences, 2007 (Product description only).
Kaschke, M., et al., "Optical Devices in Ophthalmology and Optometry", Wiley-VCH, 2014 (product description only).
PCT International Search Report issued for PCT/EP2018/051715, dated Jul. 27, 2018.
PCT International Search Report issued for PCT/EP2018/051715, dated Jun. 5, 2018.
Enders, Roland: "Die Optik des Auges und der Sehhilfen" Optische Fachveröffentlichung GmbH, Heidelberg, 1995, pp. 25 ff. (English Machine Translation also attached).

* cited by examiner

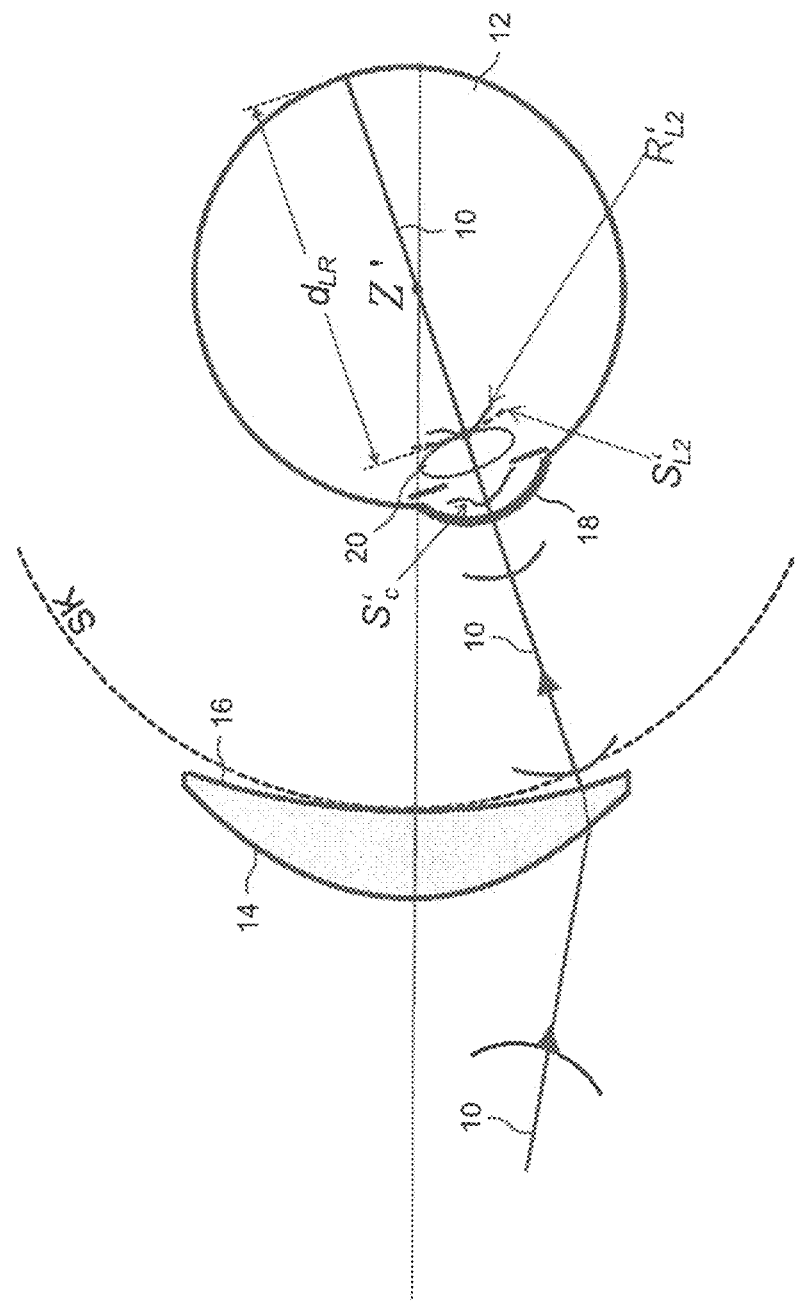

POPULATION OF AN EYE MODEL USING MEASUREMENT DATA IN ORDER TO OPTIMIZE SPECTACLE LENSES

TECHNICAL FIELD

The present invention relates, in a first approach, to a method, a device, and a corresponding computer program product for determining relevant personalized parameters of at least one eye of a spectacles wearer for the calculation or optimization of a spectacles lens for the at least one eye of said spectacles wearer, or to a corresponding method, device, and computer program product for calculating (optimizing) and producing a spectacle lens with the aid of a semi-personalized eye model. In a second approach, the present invention relates to a method, a device, and a corresponding computer program product for calculating (optimizing) and producing a spectacle lens with the aid of a semi-personalized eye model.

BACKGROUND

For the production or optimization of spectacles lenses, in particular of personalized spectacles lenses, each spectacles lens is manufactured so that an optimally good correction of a retraction error of the respective eye of the spectacles wearer is achieved for every desired viewing direction or every desired object point. In general, a spectacles lens is considered to be fully corrective for a given viewing direction if the values for sphere, cylinder, and axis of the wavefront upon passing the vertex sphere agree with the values for sphere, cylinder, and axis of the prescription for the ametropic eye. In the determination of refraction for an eye of the spectacles wearer, dioptic values (in particular sphere, cylinder, axis position—thus in particular spherocylindrical deviations) are determined for a far (normally infinite) distance, and possibly (for multifocal lenses or progressive lenses) an addition or a complete near refraction are determined for a near distance (for example according to DIN 58208). Given modern spectacles lenses, object distances deviating from the norm which would be used in the refraction determination may also be additionally specified. The prescription (in particular sphere, cylinder, axis position, and if applicable addition or post-refraction) is therefore established that is sent to a manufacturer of spectacles lenses. Knowledge of a specific or personalized anatomy of the respective eye, or of the actual refractive powers of the ametropic eye that are present in the individual instance, is not necessary for this.

However, in a normal instance a complete correction for all viewing directions simultaneously is not possible. Therefore, spectacles lenses are manufactured such that they for the most part produce a good correction of ametropias of the eye and only slight aberrations in the primary usage regions, in particular in the central viewing regions, whereas larger aberrations are permitted in peripheral regions.

In order to be able to manufacture a spectacles lens, a calculation of the spectacles lens surfaces, or of at least one of the spectacles lens surfaces, first takes place such that the desired distribution of the unavoidable aberrations is produced. This calculation and optimization typically takes place by means of an iterative variation method, via minimization of an objective function. As an objective function, in particular a function F with the following functional correlation to the spherical effect S, to the absolute value of the cylindrical effect Z, and to the axis position of the cylinder α (also referred to as an "SZA" combination) is considered and minimized:

$$F = \sum_{i=1}^{m} [g_{i,S\Delta}(S_{\Delta,i} - S_{\Delta,i,target})^2 + g_{i,Z\Delta}(Z_{\Delta,i} - Z_{\Delta,i,target})^2 + \ldots]$$

In the objective function F, at the evaluation locations i of the spectacles lens at least the actual refraction deficits of the spherical effect $S_{\Delta,i}$, and the cylindrical effect $Z_{\Delta,i}$, as well as target specifications for the refraction deficits of the spherical effect $S_{\Delta,i,target}$ and the cylindrical effect $Z_{\Delta,i,target}$ are thereby taken into account.

In DE 103 13 275, it has already been recognized that it is advantageous to specify the target specifications not as absolute values of the properties to be optimized, but rather as their deviations from the prescription, thus the required local error adaptation. This has the advantage that the target specifications are independent of the prescription ($Sph_V$, $Zyl_V$, $Axis_V$, $Pr_V,B_V$), and the target specifications do not need to be changed for every personalized prescription. It is thus also not absolute values of these optical properties, but rather the deviations from the prescription, that enter into the objective function as "real" values of the properties to be optimized. This has the advantage that the target specifications may be provided independently of the prescription, and do not need to be changed for every personalized prescription.

The respective refraction deficits at the respective assessment locations are preferably taken into account with weighting factors $g_{i,S\Delta}$ or $g_{i,Z\Delta}$. The target specifications for the refraction deficits of the spherical effect $S_{\Delta,i,target}$ and/or the cylindrical effect $Z_{\Delta,i,target}$, in particular together with the weighting factors $g_{i,S\Delta}$ or $g_{i,Z\Delta}$, thereby form what is known as the spectacles lens design. Moreover, additional residuals, in particular additional variables to be optimized, for example coma and/or spherical aberration and/or prism and/or magnification and/or anamorphic distortion etc. may in particular be taken into account, which is indicated in particular by the expression "+ . . . " in the aforementioned formula for the objective function F.

In some instances, it may contribute to a notable improvement, in particular of a personalized adaptation of a spectacles lens, if not only aberrations up to the second order (sphere, absolute value of the astigmatism, and axis position) but also of higher orders (for example coma, trefoil error, spherical aberration) are taken into account in the optimization of the spectacles lens.

From the prior art, it is known to determine the shape of a wavefront for optical elements, and in particular for spectacles lenses that are bounded by at least two refringent, refractive interfaces. For example, this may take place via numerical calculation of a sufficient number of adjacent rays, connected with a subsequent fit of the wavefront via Zernike polynomials. Another approach is based on a local wavefront calculation upon refraction (see WO 2008/089999 A1). Only a single ray (the principal ray) is hereby calculated per observation point, and accompanying are the derivatives of the pitches of the wavefront according to the transversal (orthogonal to the principal ray) coordinates. These derivatives may be formed up to a defined order, wherein the second derivatives describe the local curvature properties of the wavefront (for example refractive power, astigmatism), and the higher derivatives coincide with the higher-order aberrations.

Given a calculation of light through a spectacles lens, the local derivatives of the wavefront are calculated at a suitable position in the ray path in order to compare them there with desired values that arise from the refraction of the spectacles lens substrate. Normally, the vertex sphere, or for example the major plane of the eye at the corresponding viewing direction, is used as such a position at which an evaluation of the wavefronts occurs. It is thereby assumed that a spherical wavefront emanates from the object point and propagates up to the first spectacles lens surface. There the wavefront is refracted and subsequently propagates to the second spectacles lens surface, where it is refracted again. The last propagation then occurs from the second interface up to the vertex sphere (or the major plane of the eye), where the wavefront is compared with predetermined values for the correction of the refraction of the eye of the spectacles lens.

In order to perform this comparison on the basis of the determined refraction data of the respective eye, the evaluation of the wavefront at the vertex sphere will assume an established model of the ametropic eye in which an ametropia (refraction deficit) is superimposed on a right-sighted basic eye. This has especially proven itself, since further knowledge about the anatomy or optics of the respective eye (for example distribution of the refractive powers, eye length, longitudinal ametropia and/or refractive power ametropia) are not required for this. Detailed descriptions of this model made up of spectacles lens and refraction deficit are contained in, for example, Dr. Roland Enders "Die Optik des Auges und der Sehhilfen" ["The Optics of the Eye and Visual Aids"], Optische Fachveröffentlichung GmbH, Heidelberg, 1995, Page 25 ff., and in Diepes, Blendowske "Optik und Technik der Brille" ["Optics and Engineering of Spectacles"], Optische Fachveröffentlichung GmbH, Heidelberg, 2002, Page 47 ff. In particular, the correction model according to REINER that is described therein is used as a proven model.

The deficit or the excess of refractive power of the optical system of the ametropic eye, in comparison to an equally long right-sighted eye (residual eye) is thereby considered to be a refraction deficit. The refractive power of the refraction deficit is in particular approximately equal to the far point refraction with negative algebraic sign. For a complete correction of the ametropia, the spectacles lens and the refraction deficit together form a telescopic system (afocal system). The residual eye (ametropic eye without introduced refraction deficit) is assumed to be right-sighted. A spectacles lens thereby applies as a full correction for distance if its image-side focal point coincides with the far point of the ametropic eye, and therefore also with the object-side focal point of the refraction deficit.

SUMMARY

It is the object of the invention to improve the calculation or optimization of a spectacles lens, preferably of a progressive spectacles lens, wherein the spectacles lens is already very effectively adapted, with simple measurements of personalized data, optical data, and anatomical data of the eye, to the personalized requirements of the spectacles wearer. This object is achieved via a computer-implemented method, a device, a computer program product, a storage medium, and a corresponding spectacles lens having the features indicated in the independent claims. Preferred embodiments are the subject matter of the dependent claims.

The invention thus in particular relates to the two following approaches, which are described in detail:
First Approach Aspects of the first approach of the invention are initially described in the following paragraphs, insofar as is not explicitly noted otherwise:

In the first approach, according to a first aspect the invention thus offers a computer-implemented method for determining relevant personalized parameters of at least one eye of a spectacles wearer for the calculation or optimization of a spectacles lens for the at least one eye of the spectacles wearer. In one aspect, the invention thereby offers in particular a method for calculating or optimizing a spectacles lens for at least one eye of a spectacles wearer using the determined personalized parameters. For this purpose, personalized refraction data of the at least one eye of the spectacles wearer are initially provided. These personalized refraction data are thereby based on a personalized refraction determination. The refraction data thereby include at least the spherical and astigmatic ametropia of the eye. In a preferred embodiment, the detected refraction data also describe higher-order aberrations (HOA). The refraction data (also referred to as aberrometric data, in particular insofar as they include higher-order aberrations) are preferably measured by, for example, optometrists by means of an autorefractometer or an aberrometer (objective refraction data). Alternatively or additionally, a subjectively determined refraction may also be used. The refraction data are subsequently preferably transmitted to a spectacles lens manufacturer and/or provided to a calculation or optimization program. They are therefore provided in order to be recorded for the method according to the invention, in particular in order to be read out or received in digital form.

The provision of the personalized refraction data preferably includes a provision or determination of the vergence matrix $S_M$ of the ametropia of the at least one eye. The vergence matrix thereby describes a wavefront in front of the eye of the light outbound from a point on the retina, or of the light converging at a point on the retina. For example, such refraction data may be determined by means of measurement in that a point on the retina of the spectacles wearer is illuminated by means of a laser, from which point light then propagates. While the light from the illuminated point initially diverges essentially spherically in the vitreous body of the eye, the wavefront may vary upon traversing the eye, in particular at optical interfaces in the eye (for example the ocular lens and/or the cornea). The refraction data of the eye thus can be measured by measuring the wavefront in front of the eye.

Moreover, the method according to the first aspect of the invention includes an establishment of a personalized eye model which establishes, in a personalized manner, at least certain specifications regarding geometric and optical properties of a model eye. In the personalized eye model according to the invention, at least one shape (topography) of an anterior corneal surface of the model eye; a cornea-lens distance $d_{CL}$ (thus distance between the cornea and an anterior lens surface of the model eye is also referred to as an anterior chamber depth); parameters of the lens of the model eye which in particular at least partially establish the optical effect of the lens of the model eye; and a lens-retina distance $d_{LR}$ (thus distance between the lens, in particular the posterior lens surface, and the retina of the model eye is also referred to as a vitreous cavity length) are namely established such that the model eye has the provided personalized refraction data, meaning that a wavefront departing from a point of the retina of the model eye coincides with the wavefront determined (for example measured or otherwise determined) for the real eye of the spectacles wearer (up to a desired precision). For example, either geometric parameters (shape of the lens surfaces and their distance) and preferably material parameters (for example refractive indices of the individual components of the model eye) may be established so completely, as parameters of the lens of the model eye (lens parameters), that these at least partially establish an optical effect of the lens. Alternatively or additionally, parameters that directly describe the optical effect of the lens of the model eye may also be established as lens parameters.

In the simplest instance of an eye model, the refraction of the eye is thus determined via the optical system comprised of the anterior corneal surface, the eye lens, and the retina. In this simple model, the optical refraction at the anterior corneal surface and the refractive power of the eye lens (preferably including the spherical and astigmatic aberrations and higher-order aberrations), together with their positioning relative to the retina, establish the refraction of the model eye.

The individual variables (parameters) of the model eye are thereby accordingly established using personalized measured values for the eye of the spectacles wearer, and/or using standard values, and/or using the provided personalized refraction data. In particular, some of the parameters (for example the topography of the anterior corneal surface and/or the anterior chamber depth and/or at least one curvature of the lens surface etc.) may be provided directly as personalized measured values. Other values may be adopted from values of standard models for a human eye, in particular when these involve parameters whose personalized measurement is very complicated. Overall, however, not all (geometric) parameters of the model eye need to be provided from personalized measurements or from standard models. Rather, within the scope of the invention, a personalized adaptation for one or more (free) parameters is performed via calculation under consideration of the predetermined parameters, such that the model eye that then results has the provided personalized refraction data. Accordingly many (free) parameters of the eye model may be adapted (fitted) in a personalized manner depending on the number of parameters contained in the provided personalized refraction data. In a deviation from a model proposed in WO 2013/104548 A1, for example, within the scope of the present invention at least the lens-retina distance is established via calculations.

For the calculation or optimization of the spectacles lens, a first surface and a second surface of the spectacles lens are in particular predetermined as start surfaces with a predetermined (personalized) position relative to the model eye. In a preferred embodiment, only one of the two surfaces is optimized. It is hereby the posterior surface of the spectacles lens. A corresponding start surface is preferably thereby predetermined for both the anterior surface and the posterior surface of the spectacles lens. In a preferred embodiment, however, only one surface is iteratively varied or optimized during the optimization method. The other surface of the spectacles lens may be a simple spherical or rotationally symmetrical aspherical surface, for example. However, it is also possible to optimize both surfaces.

Based on the two predetermined surfaces, the method for calculation or optimization includes a determination of the path of a principal ray through at least one observation point (i) of at least one surface of the spectacles lens that is to be calculated or optimized in the model eye. The principal ray describes the geometric ray path, starting from an object point, through the two spectacles lens surfaces, the anterior corneal surface, and the lens of the model eye, preferably up to the retina of the model eye.

Moreover, according to the first aspect of the invention the method for calculation or optimization includes an evaluation of an aberration of a wavefront along the principal ray, said wavefront resulting from a spherical wavefront striking the first surface of the spectacles lens, at an evaluation surface, in particular in front of or inside the model eye, in comparison to a wavefront converging at a point on the retina of the eye model (reference light).

In particular, for this purpose a spherical wavefront ($w_0$) striking the first surface (anterior surface) of the spectacles lens along the primary ray is predetermined. This spherical wavefront describes the light emanating from an object point (object light). The curvature of the spherical wavefront upon striking the first surface of the spectacles lens corresponds to the reciprocal value of the object distance. The method thus preferably includes a predetermination of an object distance model which associates an object distance with each viewing direction or each observation point of the at least one surface of the spectacles lens that is to be optimized. The personalized usage situation in which the spectacles lens to be produced should be used is therefore preferably described.

The wavefront striking the spectacles lens is now preferably refracted for the first time at the anterior surface of the spectacles lens. The wavefront subsequently propagates along the principal ray within the spectacles lens, from the anterior surface to the posterior surface, where it is refracted for a second time. The wavefront transmitted through the spectacles lens now preferably propagates further along the principal ray up to the anterior corneal surface of the eye, wherein it is preferably refracted again. The wavefront is preferably also refracted again after a further propagation within the eye up to the eye lens, in order to ultimately preferably propagate up to the retina of the eye. Depending on optical properties of the personalized optical elements (spectacles lens surfaces, anterior conical surface, eye lens), each refraction event also leads to a deformation of the wavefront.

In order to achieve an exact mapping of the object point to an image point on the retina, the wavefront would preferably need to leave the eye lens as a converging spherical wavefront whose curvature corresponds precisely to the reciprocal of the distance to the retina. A comparison of the wavefront leaving from the object point with a wavefront converging (in the ideal instance of a perfect mapping) at a point on the retina (reference light) thus allows the evaluation of an incorrect adjustment. This comparison, and therefore the evaluation of the wavefront of the object light in the personalized eye model, may thereby take place at different locations along the path of the principal ray, in particular between the second surface of the optimized spectacles lens and the retina. In particular, the evaluation surface may therefore be situated at different positions, in particular between the second surface of the spectacles lens and the retina. The refraction and propagation of the light leaving the object point is preferably calculated accordingly broadly for each visual point in the personalized eye model. The evaluation surface may relate either to the actual ray path or to a virtual ray path as is utilized for the construction of the exit pupil AP, for example. In the event of the virtual ray path, after refraction the light must be propagated back through the posterior surface of the eye lens, up to a desired plane (preferably up to the plane of the AP), wherein the refractive index that is thereby utilized must correspond to the medium of the vitreous body and not, for instance, to the eye lens. In the event that the evaluation surface is provided behind the lens, or after the refraction at the posterior lens surface of the model eye, or in the event that the evaluation surface is achieved via back-propagation along a virtual ray path (as in the instance of the AP), the resulting wavefront of the object light may preferably simply be compared with a spherical wavefront of the reference light. For this, the method thus preferably includes a predetermination of a spherical wavefront striking the first surface of the spectacles lens; a determination of a wavefront resulting from the spherical wavefront in the at least one eye due to the effect of at least the first and second surface of the spectacles lens, the anterior corneal surface, and the lens of the model eye; and an evaluation of the aberration of the resulting wavefront in comparison to a spherical wavefront converging on the retina.

If, by contrast, an evaluation surface should be provided within the lens or between the lens of the model eye and the spectacles lens to be calculated or optimized, a reverse propagation from a point on the retina through the individual components of the model eye, up to the evaluation surface, is simply simulated as a reference light in order to produce there a comparison of the object light with the reference light.

However, as has already been mentioned above, a complete correction of the refraction of the eye for all viewing directions of the eye simultaneously, thus for all visual points of the at least one spectacles lens surface that is to be optimized, is generally not possible. Depending on the viewing direction, a deliberate incorrect adjustment of the spectacles lens is thus preferably provided which, depending on the use situation, is small in particular in the primarily used regions of the spectacles lens (for example central visual points), somewhat greater in the less used regions (for example peripheral visual points). This procedure is already known in principle from conventional optimization methods.

In order to optimize the spectacles lens, the at least one surface of the spectacles lens that is to be calculated or optimized is iteratively varied until an aberration of the resulting wavefront corresponds to a predetermined target aberration, thus in particular deviates by predetermined values of the aberration from the wavefront of the reference light (for example a spherical wavefront whose center of curvature lies on the retina). Here the wavefront of the reference light is also referred to as a reference wavefront. For this purpose, the method preferably includes a minimization of an objective function F, in particular analogous to the objective function already described above. In the event that a propagation of the object light up to the retina is calculated, an evaluation may be performed there instead of a comparison of wavefront parameters, for example by means of what is known as a "point spread function".

Within the scope of the present invention, it has thus been proposed to establish such a personalized eye model, in particular for the calculation or optimization of a spectacles lens, which is adapted in a personalized manner to the individual spectacles wearer up to the retina, in that at least the vitreous body length of the model eye is calculated in a personalized manner depending on other personalized determined data, in particular measured data, of the eye. This parameter therefore needs neither to be established a priori nor be directly measured. Within the scope of the present invention, it has turned out that this therefore produced a noteworthy improvement in the personalized adaptation given a comparably small expenditure, because the wavefront calculation turns out to be very sensitively dependent on this length parameter.

The personalized calculation of the eye model, in particular of the lens-retina distance (vitreous body length), may thereby in particular already be performed in an aberrometer or a topograph with accordingly expanded functionality. A personalized determination of an eye length thereby preferably takes place. The calculated vitreous body length, and/or the determined (calculated eye length), is particularly preferably displayed. For this purpose, a corresponding device (in particular an aberrometer or topograph) has a corresponding display device.

The anterior corneal surface is thereby preferably measured in a personalized manner, and the eye lens of the personalized eye model is accordingly calculated in order to satisfy the personalized determined refraction data. In a preferred embodiment, the anterior corneal surface (or its curvature) is thereby measured in a personalized manner along the principle section (topometry). In a further preferred embodiment, the topography of the anterior corneal surface (meaning the complete description of the surface) is measured in a personalized manner. In a further preferred embodiment, the establishment of the cornea-lens distance takes place using personalized measured values for the cornea lens distance.

The establishment of the parameters of the lens of the model eye particularly preferably includes an establishment of the following parameters:
a shape of the anterior lens surface;
a lens thickness; and
a shape of the posterior lens surface.

Even if it is not essential for the use of the invention, the personalized adaptation may again be improved via this more precise model of the lens.

In this instance, in a particularly preferred embodiment the establishment of the lens thickness and of the shape of the posterior lens surface takes place using predetermined values (standard values, for example from the specialist literature), wherein the establishment of the shape of the anterior lens surface further preferably includes:
provision of standard values for a mean curvature of the anterior lens surface; and
calculation of the shape of the anterior lens surface under consideration of the provided personalized refraction data.

In a further preferred embodiment of the more detailed lens model, the establishment of the shape of the anterior lens surface includes:
provision of a personalized measured value of a curvature in a normal section of the anterior lens surface.

In this instance, it is particularly preferred if the establishment of the lens thickness and of the shape of then posterior lens surface moreover takes place using standard values, and even more preferably the establishment of the shape of the anterior lens surface includes:
calculation of the shape of the anterior lens surface under consideration of the provided personalized refraction data, and of the provided personalized measured value of the curvature in a normal section of the anterior lens surface.

As an alternative or in addition to the shape of the lens or of the lens surfaces, the establishment of the lens parameters may include an establishment of an optical effect of the lens. In particular, a position of at least one principal plane and a spherical effect (or at least a focal width) of the lens of the model eye are thereby established. A cylindrical effect (magnitude and axis length) of the lens of the model eye is also particularly preferably established. In a further preferred embodiment, optical higher-order aberrations of the lens of the model eye may also be established.

The evaluation surface preferably lies between the anterior corneal surface and the retina. In a particularly preferred embodiment, the evaluation surface lies between the lens and the retina of the model eye. In another particularly preferred embodiment, the evaluation surface lies at the exit pupil (AP) of the model eye. The exit pupil may thereby be situated before the posterior lens surface of the model eye. Given this positioning, a particularly precise, personalized adaptation of the spectacles lens may be achieved.

In a further aspect, the invention offers a device to determine relevant personalized parameters of at least one eye of a spectacles wearer for the calculation or optimization of a spectacles lens for the at least one eye of the spectacles wearer. In one aspect, the invention thereby in particular offers a device for calculating or optimizing a spectacles lens for at least one eye of a spectacles wearer using the determined personalized parameters. The device for determining relevant personalized parameters comprises:
 a data interface for providing personalized refraction data of the at least one eye of the spectacles wearer; and
 a modeling module to establish a personalized eye model based on at least the parameters
  shape of an anterior corneal surface of a model eye;
  cornea-lens distance;
  parameters of the lens of the model eye; and
  lens-retina distance
are established using personalized measured values for the eye of the spectacles wearer and/or using standard values and/or using the provided personalized refraction data, such that the model eye has the provided personalized refraction data, wherein at least the establishment of the lens-retina distance takes place via calculation.

The modeling module is preferably designed to determine an eye length of the model eye under consideration of the calculated lens-retina distance. The device moreover preferably comprises a display device to display the calculated lens-retina distance and/or the determined eye length. The device is particularly preferably designed as an aberrometer and/or as a topograph.

Moreover, the device for calculating or optimizing a spectacles lens comprises in particular:
 a surface model database to predetermine a first surface and a second surface for the spectacles lens to be calculated or optimized;
 a principal ray determination module to determine the path of a principal ray through at least one visual point (i) of at least one surface of the spectacles lens in the model eye, which surface is to be calculated or optimized;
 an evaluation module to evaluate an aberration of a wavefront at an evaluation surface, said wavefront resulting along the principal ray from a spherical wavefront striking the first surface of the spectacles lens, in comparison to a wavefront converging at a point on the retina of the eye model; and
 an optimization module iteratively varies the at least one surface of the spectacles lens, said surface to be calculated or optimized, until the evaluated aberration corresponds to a predetermined target aberration.

Moreover, the invention offers a computer program product, in particular in the form of a storage medium or a data stream, which contains program code that is designed to implement a method for determining relevant personalized parameters of at least one eye of a spectacles wearer, and/or a method for calculating or optimizing a spectacles lens according to the present invention, in particular in a preferred embodiment, when loaded and executed on a computer.

Second Approach

Insofar as is not explicitly noted otherwise, aspects of the second approach of the invention are described in the following paragraphs:

In the second approach, according to a first aspect the invention thus offers a computer-implemented method for determining personalized aberration data of at least one eye of a spectacles wearer, in particular for a use for calculation or optimization of a spectacles lens for the at least one eye of the spectacles wearer. For this purpose, a measured corneal topography of the at least one eye of the spectacles wearer is initially provided. This corneal topography is preferably measured directly by means of a corresponding topograph. Alternatively, such measured data may also be stored in order to be able to provide them later for further processing, for example.

Starting from the measured corneal topography, personalized imaging properties of the cornea of the eye are determined which describe at least higher-order aberrations of the cornea, $HOA_C$. These personalized imaging properties of the cornea may be determined from the corneal topography and under consideration of a refractive index transition between air and cornea. The personalized imaging properties may in the course of this be determined, and possibly stored, in a desired parameter presentation in the form of different components. Personalized imaging properties in particular describe different components of the optical light refraction, for example a spherical portion, astigmatic portion, and portions of the higher-order aberrations (i.e. aberrations greater than the second order); according to the invention, at least (some) higher-order aberrations of the cornea (as at least a portion of the personalized imaging properties of the cornea) are determined.

According to the invention, at least higher-order aberrations of the eye, $HOA_C$, are then determined under consideration of the determined personalized imaging properties of the cornea of the eye, in particular under consideration of the higher-order aberrations of the cornea, $HOA_{Eye}$. In particular, these higher-order aberrations of the eye, $HOA_{Eye}$, are represented or determined as aberrations of a wavefront at the cornea that converges at a point on the retina after a refraction at the anterior corneal surface with the measured topography (and, if applicable, a further propagation through the eye). The higher-order aberrations of the eye are thereby determined under consideration of the determined personalized imaging properties of the cornea of the eye, thus under consideration of the personalized measurement of the corneal topography, but not under consideration of personalized measurements of (higher-order) aberrations of other components of the eye (for example the eye lens).

In the calculation or optimization of spectacles lenses, the consideration of higher-order aberrations is in fact definitely beneficial to the quality of the personalized adaptation of a spectacles lens. However, it is often costly to measure the higher-order aberrations of an eye in a personalized manner. For example, not every optometrist has available a corresponding aberrometer with which these aberrations can be detected directly and simply. However, with the present invention it is nevertheless possible to provide a calculation or optimization of a spectacles lens under consideration of HOAs without needing to measure the HOAs of the entire eye directly and in a personalized manner. For this purpose, in a subsequently described eye model, higher-order aberrations for interfaces and optical properties of individual components in the model eye may be taken into account. However, the personalized determination of the HOAs of the entire eye, and possibly a population of the parameters of the eye model, takes place not using personalized measurements of the HOAs of the entire eye, but rather using personalized measurement of the HOAs of the cornea of the eye. In particular, for this purpose the method includes a provision of personalized aberrations of the cornea of the eye of the spectacles wearer which describe higher-order aberrations (HOA) of the cornea of the eye. In particular, for this purpose the shape of the anterior corneal surface may be measured, which is normally possibly significantly more simply than directly measuring the HOAs of the entire eye.

In a preferred embodiment, the determination of personalized imaging properties of the cornea of the eye includes a determination of values of higher-order aberrations of the cornea, $HOA_C$, wherein the determination of the aberrations of the eye preferably includes a determination of higher-order aberrations of the eye, $HOA_{Eye}$, according to $HOA_{Eye}=HOA_C+\Delta HOA_{C,Eye}$, with a higher-order displacement, $\Delta HOA_{C,Eye}$, that is predetermined or determined in a personalized manner, in particular with $\Delta HOA_{C,Eye}=0$. The aberrations of the entire eye, or a good approximation thereof, can therefore be determined very quickly and effectively with simple means.

Independently of the concrete, functional correlation, in general $\Delta HOA_{C,Eye}$ preferably acts as an effective variable for describing the higher-order aberrations of the residual eye, in particular in the event that not all higher-order aberrations of the entire eye can be explained or described via the higher-order aberrations of the cornea. In particular, in general the anterior lens surface and/or the posterior lens surface in the residual eye possess higher-order aberrations. How these compound with the higher-order aberrations of the cornea to form aberrations of the entire eye also depends in particular on dimensions of the eye, for example the length parameters $d_{CL}$, $d_L$, and/or $d_{LR}$ of the eye that are still be described in the following. Such correlations might be adapted from, for example, Esser, W. Becken, W. Müller, P. Baumbach, J. Arasa and D. Utlenweiler, "Derivation of the Refraction Equations for Higher Order Aberrations of Local Wavefronts at Oblique Incidence", JOSA A Vol. 27, No. 2, P 218-37 (2010); and/or from G. Esser, W. Becken, W. Müller, P. Baumbach, J. Arasa and D. Utlenweiler, "Derivation of the Propagation Equations for Higher Order Aberrations of Local Wavefronts", JOSA A Vol. 28, No. 12, P 2442-58 (2011).

In one embodiment, the method for determining personalized aberration data includes a determination or provision of correction values $\Delta HOA_{C,Eye,Anteriorlenssurface}$ of higher-order aberrations due to the anterior lens surface; a determination or provision of correction values $\Delta HOA_{C,Eye,Posteriorlenssurface}$ of higher-order aberrations due to the posterior lens surface; and a determination or provision of length parameters of the eye; wherein the determination of the personalized imaging properties of the cornea of the eye includes a determination of values of the higher-order aberrations of the cornea, $HOA_C$ and the determination of the aberrations of the eye preferably includes a determination of higher-order aberrations of the eye, $HOA_{Eye}$, according to $$HOA_{Eye}=f(HOA_C, \Delta HOA_{C,Eye,Anteriorlenssurface}, \Delta HOA_{C,Eye,Posteriorlenssurface}, \text{Lengthparameter}).$$

If it is not desired to break down the components of the eye in detail according to refractive surfaces, all parameters of the residual eye may then also be approximately combined into $$HOA_{C,Auge}=h(\Delta HOA_{C,Eye,Anteriorlenssurface}, \Delta HOA_{C,Eye,Posteriorlenssurface}, \text{Lengthparameter}).$$

and then the higher-order aberrations of the entire eye may be generally written as $$HOA_{Eye}=g(HOA_C, \Delta HOA_{C,Eye}).$$

It is thereby to be taken into account that all parameters except for $HOA_C$ do not necessarily need to be measured in a personalized manner, but rather may also be taken from the literature or be model-based, also assumed depending on other variables (for example eye length from LOAs from the subjective refraction, and if applicable $LOA_C$).

In a further preferred embodiment, the determination of the personalized imaging properties of the cornea of the eye includes a determination of lower-order refraction values of the cornea, $LOA_C$, wherein the determination of the aberrations of the eye includes a determination of lower-order aberrations of the eye, $LOA_{Eye}$, according to $LOA_{Eye}=LOA_C+\Delta LOA_{C,Eye}$, with a predetermined or personalized determined lower-order displacement, $\Delta LOA_{C,Eye}$.

This preferred embodiment relates, for example, to the situation that the LOAs of the eye are also not directly measured (for example per refraction), but rather like the HOAs are estimated or approximated from the topography measurement. In a preferred embodiment, both LOAs and HOAs of the eye are given directly by the corresponding corneal aberrations, except for a shift $\Delta LOA_{C,Eye}$ or $\Delta HOA_{C,Eye}$. This may be constant or depend on additional parameters. $\Delta HOA_{C,Eye}=0$ is preferred for all orders n>2, and $\Delta LOA_{C,Eye,M}=-LOA_{C,M,Std}$, $\Delta LOA_{C,Eye,J0}=0$, $\Delta LOA_{C,Eye,J45}=0$, wherein $\Delta LOA_{C,Eye,M}$, $\Delta LOA_{C,Eye,J0}$, $\Delta LOA_{C,Eye,J45}$ are those shifts that relate to the M-component, the $J_0$-component, or the $J_{45}$-component of the aberrations of the eye, and wherein $LOA_{C,M,Std}$ is the standard value of the M-component of the cornea, which is preferably $\Delta LOA_{C,M,Std}=43.08$ dpt.

In a preferred embodiment, the determination of lower-order refraction values of the cornea, $LOA_C$, includes a determination of astigmatic portions of the refraction of the cornea, $LOA_{C,J0}$ and $LOA_{C,J45}$, wherein the determination of lower-order aberrations of the eye, $LOA_{Eye}$, includes a determination of astigmatic portions of the lower-order aberrations of the eye, $LOA_{Eye,J0}$ and $LOA_{Eye,J45}$, according to $LOA_{Eye,J0}=LOA_{C,J0}$ and $LOA_{Eye,J45}=LOA_{C,J45}$. Alternatively or additionally, the determination of lower-order refraction values of the cornea, $LOA_C$, preferably includes a determination of a spherical portion of the refraction of the cornea, $LOA_{C,M}$, wherein the determination of lower-order aberrations of the eye, $LOA_{Eye}$, preferably includes a determination of a spherical portion of the lower-order aberration of the eye, $LOA_{Eye,M}$, according to $LOA_{Eye,M}=LOA_{C,M}-LOA_{C,M,Std}$, with a predetermined standard value $LOA_{C,M,Std}$.

Furthermore, shifts are preferred that are themselves a function of the corneal topography. A shift is particularly preferred in which the M-component of the LOAs of the eye is a linear function $\Delta LOA_{C,Eye,M}(LOA_{C,M})=\Delta LOA_{C,Eye,M}(LOA_{C,M,Std})+\alpha(LOA_{C,M}-LOA_{C,M,Std})$ of the M-component of the LOAs of the cornea, wherein $5<\alpha<15$ is preferred. The determination of lower-order refraction values of the cornea, $LOA_C$, thus includes a determination of a spherical portion of the refraction of the cornea, $LOA_{C,M}$, wherein the determination of lower-order aberrations of the eye, $LOA_{Eye}$, includes a determination of a spherical portion of the lower-order aberrations of the eye, $LOA_{Eye,M}$, according to $LOA_{Eye,M}=LOA_{C,M}+\Delta LOA_{C,Eye,M}(LOA_{C,M})$, with a linear function $\Delta LOA_{C,Eye,M}(LOA_{C,M})=\Delta LOA_{C,Eye,M}(LOA_{C,M,Std})+\alpha(LOA_{C,M}-LOA_{C,M,Std})$ having a predetermined standard value $LOA_{C,M,Std}$ and a predetermined value α, preferably in a range of 5<α<15.

In a further preferred embodiment, the determination of the aberrations of the eye includes a determination of lower-order aberrations of the eye, $LOA_{Eye}$, using personalized refraction measurements at the at least one eye. For this purpose, in particular personalized refraction data of the at least one eye of the spectacles wearer are thus provided. These personalized refraction data are thereby based on a personalized refraction determination. The refraction data thereby in particular include the spherical and astigmatic ametropia of the eye. However, the personalized refraction data contain no personalized higher-order aberrations (HOA) of the eye.

Within the scope of the present specification, the differentiation between lower-order aberrations (LOA) and higher-order aberrations (HOA) takes place in the manner typical to this field, so that lower-order aberrations refer to the aberrations up to the 2nd order of a Taylor or Zernike expansion (in particular prism, sphere, cylinder, axis length), whereas higher-order aberrations relate to the aberrations as of the 3rd order in a Taylor or Zernike expansion.

The refraction data are preferably measured by means of an autorefractometer, for example by an optometrist (objective refraction data). Alternatively or additionally, a subjectively determined refraction may also be used. The refraction data are subsequently preferably sent to a spectacles lens manufacturer and/or provided to a calculation or optimization program. They are therefore also provided in order to be recorded for the method according to the invention, in particular are read out and/or received in digital form.

The provision of the personalized refraction data preferably includes a provision or determination of the vergence matrix $S_M$ of the ametropia of the at least one eye for lower-order aberrations, in particular up to the 2nd order of a Taylor or Zernike chart. The vergence matrix thereby describes a wavefront in front of the eye of the light leaving from a point on the retina, or a light converging at a point on the retina. In terms of measurement, such refraction data may, for example, be determined in that a point on the retina of the spectacles wearer is illuminated by means of a laser, from which point light then propagates. While the light from the illuminated point initially diverges essentially spherically in the vitreous body of the eye, the wavefront may vary upon passing through the eye, in particular at optical interfaces in the eye (for example the eye lens and/or the cornea). The refraction data of the eye can thus be measured via a measurement of the wavefront in front of the eye.

The vergence matrix coincides in a known manner with the aforementioned M-component, the $J_0$-component, and the $J_{45}$-component, in particular according to $$S = \begin{pmatrix} M+J_0 & J_{45} \\ J_{45} & M-J_0 \end{pmatrix}.$$

The LOAs of the eye are thus preferably provided as M, $J_0$, $J_{45}$, in particular in the corneal plane (for example per refraction and subsequent HSA conversion).

As has already been described, the HOAs of the eye are preferably given directly by the cornea aberrations, except for a shift $HOA_{C,Eye}$. This may be constant or depend on additional parameters. $\Delta HOA_{C,Eye}=0$ is preferred for all orders n>2.

In further embodiments, an eye model is preferably introduced. In a simple instance, the eye lens is thereby modeled not by two surfaces, but rather by a single lens whose LOAs and HOAs are given by $LOA_L$ or $HOA_L$. This simple instance may be produced from the embodiments described further in the following, in which it is set that: $d_L=0$ $L=L_1+L_2$. The function of how the lens then arises from the $LOA_C$, corresponding to formulas (4) and (5) from the specification WO 2013/104548 A1, if $d_L=0$ $L=L_1+L_2$ is also set there, reads $$L(M, J_0, J_{45}, LOA_C, d_{CL}, d_{LR}) = \frac{n_{LR}}{d_{LR}}1 - \frac{S+C}{1-d_{CL}/n_{CL}(S+C)} \text{ wherein}$$

$$S = \begin{pmatrix} M+J_0 & J_{45} \\ J_{45} & M-J_0 \end{pmatrix}$$

is in turn the matrix representation of the refraction, and C is the corresponding matrix representation for $LOA_C$.

The HOAs of the entire eye are then determined according to a function $f(LOA_C, HOA_C, L, HOA_L, d_{CL}, d_{LR})$, which materializes in that a spherical wave propagates backward through the eye, beginning at a point on the retina, and is refracted. The HOAs of the resulting wavefront, in particular in the plane of the cornea, are then the HOAs of the entire eye.

The determination of aberrations of the eye thus preferably includes:
   establishment of a personalized eye model in which a shape of an anterior corneal surface of a model eye corresponds to the measured corneal topography, and in which moreover at least
   a cornea-lens distance;
   parameters of a lens of the model eye; and
   a lens-retina distance
are established using personalized measured values for the eye of the spectacles wearer and/or using standard values and/or using the determined lower-order aberrations of the eye, such that the model eye has the determined lower-order aberrations of the eye; and
   determination of an aberration of a wavefront converging at a point on the retina after a refraction at the anterior corneal surface of the model eye and a propagation through the model eye.

The establishment of the parameters of the lens of the model eye particularly preferably includes an establishment of the following parameters:
   shape of the anterior lens surface;
   lens thickness; and
   shape of the posterior lens surface.

In addition to the personalized corneal topography, the refraction M, $J_0$, $J_{45}$ (or its matrix representation $$S = \begin{pmatrix} M+J_0 & J_{45} \\ J_{45} & M-J_0 \end{pmatrix})$$

and length parameters $d_{CL}, d_L, d_{LR}$ of the eye are thereby preferably provided. The LOAs of the one lens surface are therefore preferably calculated from the LOAs of the other lens surface, in that the requirement is posed that the entire eye, constructed from the components, then has the given refraction (i.e. a wavefront) that corresponds to the refraction data, propagates in a 2nd order through the eye, and converges—refracted—on the retina as a spherical wave.

The HOAs of the entire eye can then be expressed as a function $f(LOA_C, HOA_C, L_1, HOA_{L1}, L_2, HOA_{L2}, d_{CL}, d_L, d_{LR})$ that materializes in that a spherical wave propagates backward through the eye, beginning at a point on the retina, and is refracted. The HOAs of the resulting wavefront in the plane of the cornea are then the HOAs of the entire eye.

In preferred embodiments, the length parameters are constant. In further preferred variants, they are even estimated values $d_{CL}, d_L, d_{LR}$ as a function of the refraction, the LOAs of the cornea, or combinations hereof, that utilize the known correlations from the general population (for example that myopia correlates with greater eye length). Examples of this are $d_{CL}(M,C), d_{LR}(M,C)$.

Length parameters, for example $d_{LR}$, are particularly preferably calculated as described further below by way of example. Here as well, a function $d_{LR}(M,C)$ results, wherein this then does not originate from correlations within the general population for a given topography measurement, however, but rather is calculated directly from the topography measurement under specific assumptions about the lens surfaces.

The establishment of the lens thickness and of the lens-retina distance preferably takes place using predetermined standard values, wherein the establishment of the shape of the anterior lens surface and of the posterior lens surface takes place using predetermined standard values for the higher-order aberrations of the respective surface. The standard values of the higher-order aberrations of the anterior lens surface and/or of the posterior lens surface are particularly preferably set to zero.

The determination of the personalized imaging properties of the cornea of the eye preferably includes a determination of lower-order refraction values of the cornea, $LOA_C$. In particular in this instance, the establishment of the lens-retina distance and/or the establishment of the lens thickness and/or the establishment of the shape of the anterior lens surface and/or of the posterior lens surface preferably takes place using the determined lower-order refraction values of the cornea, $LOA_C$. The establishment of others of the cited values may thereby preferably take place in particular using standard values.

The determination of the aberrations of the eye preferably includes a determination of lower-order aberrations of the eye, $LOA_{Eye}$. In particular in this instance, the establishment of the lens-retina distance and/or the establishment of the lens thickness and/or the establishment of the shape of the anterior lens surface and/or of the posterior lens surface preferably takes place using the determined lower-order aberrations of the eye, $LOA_{Eye}$. The establishment of others of the cited values may thereby preferably take place in particular using standard values.

A correlation between the sphere of the eye and the lens-retina distance $d_{LR}$ is thereby preferably provided from statistical examinations of the general population, for example. A personalized value $d_{LR}$ of the lens-retina distance is therewith concluded using a personalized determined value of the sphere.

In another preferred embodiment, a correlation is provided between the sphere of the eye and the total length of the eye, for example from statistical examinations of the general population. A personalized value of the total length of the eye is therewith concluded using an value of the sphere determined in a positive manner Personalized values of the anterior chamber depth $d_{CL}$ and of the lens thickness $d_L$ are then preferably subtracted to determine the personalized lens-retina distance.

In a further preferred embodiment, the LOAs of the cornea and the personalized values of the anterior chamber depth $d_{CL}$ and of the lens thickness $d_L$ are determined and are preferably used, together with standard values for the lens curvatures, to determine the length $d_{LR}$ so that a wavefront from an infinite distance converges precisely on the retina (with regard to its LOAs) under these assumptions.

The method thus preferably includes an establishment of a personalized eye model which establishes at least certain specifications regarding geometric and optical properties of a model eye in a personalized manner. At least a shape (topography) of an anterior corneal surface of the model eye is thus established in the personalized eye model using the personalized topography measurement. Moreover, a cornea-lens distance $d_{CL}$ (this distance between the cornea and a lens or an anterior lens surface of the model eye is also referred to as an anterior chamber depth), parameters of the lens of the model eye which in particular at least partially establish the optical effect of the lens of said model eye, and a lens-retina distance $d_{LR}$ (this distance between the lens, in particular the posterior lens surface, and the retina of the model eye is also referred to as a vitreous body length) are preferably established in a defined manner, namely such that the model eye has the provided personalized refraction data, meaning that a wavefront in the model eye that emanates from a point on the retina of the model eye coincides with the wavefront determined (for example measured or otherwise determined) for the real eye of the spectacles wearer (in particular to a certain precision). Optical properties and refractive surfaces in the eye model are thereby established such that they also described higher-order aberrations (at least one).

For example, geometric parameters (shape of the lens surfaces and their distance) and preferably material parameters (for example refractive indices of the individual components of the model eye) may be completely established as parameters of the lens of the model eye (lens parameters), so that these at least partially establish an optical effect of the lens. Alternatively or additionally, parameters that directly describe the optical effect of the lens of the model eye may also be established.

In a simple instance of an eye model, the refraction of the eye is thus determined via the optical system comprising the anterior corneal surface, the eye lens, and the retina. In this simple model, the optical refraction at the anterior corneal surface and the refractive power of the eye lens (including the spherical and astigmatic aberrations, and at least one higher-order aberration), together with their positioning relative to the retina, establish the refraction of the model eye.

The individual variables (parameters) of the model eye are thereby accordingly established using personalized measured values for the eye of the spectacles wearer, and/or using standard values, and/or using the provided personalized refraction data. In particular, some of the parameters (for example the anterior chamber depth and/or at least one curvature of a lens surface etc.) may be provided directly as personalized measured values. Other values may also be adapted from values of standard models for a human eye, in particular when these involve parameters whose personalized measurement is very complicated. Overall, however, not all (geometric) parameters of the model eye need to be predetermined from personalized measurements or from standard models. Rather, a personalized adaptation for one or more (free) parameters may be performed via calculation, under consideration of the predetermined parameters, such that the model eye that then results has the provided personalized refraction data. Depending on the number of parameters contained in the provided personalized refraction data, accordingly many (free) parameters of the eye model may be adapted (fitted) in a personalized manner.

Details of a model eye which are described in the following, which model eye may be used for a calculation or optimization of a spectacles lens, in particular for a ray calculation and wavefront calculation, are preferably used analogous to a model eye for determining the personalized aberration data of the at least one eye of the spectacles wearer.

In one aspect, the invention offers the possibility to use the determined personalized aberration data in order to determine sphero-cylindrical values for at least one eye of a spectacles wearer. These then preferably serve for the selection of an anterior and/or posterior surface for a spectacles lens that is to be manufactured. It is also possible, based on predetermined anterior and/or posterior surfaces, to perform a modification of the anterior and/or posterior surface as such, or of the relative position with regard to one another, using the optimized sphero-cylindrical values, in order to then manufacture a spectacles lens based on the modification.

A computer-implemented method for determining optimized sphero-cylindrical values for at least one eye of a spectacles wearer preferably includes:
  determination of subjective sphero-cylindrical refraction values,
  determination of objective sphero-cylindrical refraction values, which includes:
    provision of personalized aberration data which have been determined by means of a method according to the present invention, in particular in one of the preferred embodiments described here;
    determination of a reference wavefront at an evaluation surface using the provided personalized aberration data of the eye;
    predetermination of a starting specification for a wavefront to be optimized, which describes objective sphero-cylindrical refraction values to be optimized, at the evaluation surface,
    determination of a difference wavefront from the wavefront to be optimized and the reference wavefront;
    evaluation of the difference wavefront using the predetermined metric (for example according to WO 2008/089999 A1);
    determination of the wavefront to be optimized, such that the evaluation of the difference wavefront satisfies predetermined target criteria; and
    determination of the objective sphero-cylindrical refraction values from the determined wavefront to be optimized; and
  determination of the optimized sphero-cylindrical values as a weighted mean value from the determined subjective sphero-cylindrical refraction values and the determined objective sphero-cylindrical refraction values.

Alternatively, the point spread function of a corresponding mapping may be considered instead of the wavefront.

Based on these optimized sphero-cylindrical values, in one aspect the invention thus offers a computer-implemented method for calculating or optimizing a spectacles lens for at least one eye of a spectacles wearer, including:
  determination of the optimized sphero-cylindrical values for at least one eye of a spectacles wearer on the basis of personalized aberration data, in particular in one of the manners described here;
  determination of a combination of anterior and posterior surface (spherical, cylindrical, aspherical, atoroidal, progressive, . . . ) on the basis of the determined optimized sphero-cylindrical values; and
  if applicable, modification of the determined anterior surface and/or posterior surface on the basis of the basis of the determined, optimized sphero-cylindrical values.

Alternatively, the method may include:
  determination of the optimized sphero-cylindrical values for at least one eye of a spectacles wearer on the basis of personalized aberration data, in particular in one of the manners described here;
  establishment of a combination of anterior and posterior surface as a starting surface; and
  modification of the anterior and/or posterior surface on the basis of the basis of the determined, optimized sphero-cylindrical values.

In a further aspect, the invention relates to a computer-implemented method for calculating or optimizing a spectacles lens for at least one eye of a spectacles wearer, including a provision of personalized aberration data which have been determined by means of a method according to the invention as described here for the determination of personalized aberration data of at least one eye of a spectacles wearer, in particular in one of the preferred embodiments as described here. In a preferred embodiment, the method for calculating or optimizing a spectacles lens includes a corresponding method for determining personalized aberration data of at least one eye of a spectacles wearer.

Moreover, the method for calculation or optimization of a spectacles lens in particular includes
  determination of a reference aberration at an evaluation surface using the provided personalized aberration data of the eye;
  predetermination of a first surface and a second surface for the spectacles lens that is to be calculated or optimized;
  determination of the path of a primary ray through at least one visual point (i) of at least one surface of the spectacles lens that is to be calculated or optimized;
  evaluation of an aberration of a wavefront at the evaluation surface, which wavefront results from spherical wavefront striking the first surface of the spectacles lens, in comparison to the determined reference aberration;
  iterative variation of the at least one surface of the spectacles lens, which surface is to be calculated or optimized, until the evaluated aberration corresponds to a predetermined target aberration.

The evaluation surface preferably lies on the vertex sphere.

For the calculation or optimization of the spectacles lens, a first surface and a second surface of the spectacles lens are thus in particular predetermined as starting surfaces with a predetermined (personalized) position relative to the model eye. In a preferred embodiment, only one of the two surfaces is optimized. It is hereby preferably the posterior surface of the spectacles lens. A corresponding starting surface is thereby preferably predetermined both for the anterior surface and for the posterior surface of the spectacles lens. In a preferred embodiment, however, only one surface is iteratively varied or optimized during the optimization method. The other surface of the spectacles lens may, for example, be a simple spherical or rotationally symmetrical aspherical surface. However, it is also possible to optimize both surfaces.

Assuming the two predetermined surfaces, the method includes a determination of the path of a primary ray through at least one visual point (i) of at least one surface of the spectacles lens in the model eye, which at least one surface is to be calculated or optimized. The primary ray describes the geometric ray path starting from an object point, through the two spectacles lens surfaces and at least the anterior corneal surface, preferably also through the lens of the model eye, in particular up to the retina of the model eye.

Moreover, the method includes an evaluation of an aberration pressure fluctuation a wavefront propagating along the principal ray at an evaluation surface within the model eye, which wavefront results from a spherical wavefront striking the first surface of the spectacles lens, in comparison to a wavefront (reference wavefront or reference light) converting at a point on the retina of the eye model. The evaluation of the aberration thereby preferably includes a comparison of at least one higher-order aberration (HOA). For this purpose, both the propagation and refraction of the spherical wavefront striking the first surface of the spectacles lens is thus calculated on the path to the eye, or in the eye, including at least one higher-order aberration; the reference wavefront is thus also provided with the at least one higher-order aberration.

In particular, for this purpose a spherical wavefront ($w_0$) striking the first surface (anterior surface) of the spectacles lens along the principal ray is predetermined. This spherical wavefront describes the light emanating from an object point (object light). The curvature of the spherical wavefront upon striking the first surface of the spectacles lens corresponds to the reciprocal of the object distance. The method thus preferably includes a predetermination of an object distance model which associates an object distance with each viewing direction or each visual point of the at least one surface of the spectacles lens that is to be optimized. The personalized usage situation in which the spectacles lens to be produced should be used is therefore preferably described.

The wavefront striking the spectacles lens is now refracted, preferably for the first time, at the anterior surface of the spectacles lens. The wavefront subsequently propagates along the primary ray within the spectacles lens, from the anterior surface to the posterior surface, where it is refracted for a second time. The wavefront transmitted through the spectacles lens now subsequently propagates further along the primary ray, up to the anterior corneal surface of the eye, wherein it is again refracted. After a further propagation within the eye, the wavefront is preferably, up to the eye lens, also refracted again there. In reality, after the refraction at the eye lens the object light propagates further up to the retina of the eye. Depending on optical properties of the individual optical elements (spectacles lens surfaces, anterior corneal surface, eye lens), each refraction event also leads to a deformation of the wavefront, wherein according to the invention at least one higher-order aberration is considered.

In order to achieve an exact mapping of the object point to an image point on the retina, the wavefront would preferably need to leave the eye lens as a converging spherical wavefront whose curvature corresponds precisely to the reciprocal of the distance to the retina. A comparison of the wavefront leaving from the object point with a wavefront converging (in the ideal instance of a perfect mapping) at a point on the retina (reference light) thus allows the evaluation of an incorrect adaptation. This comparison, and therefore the evaluation of the wavefront of the object light in the personalized eye model, takes place at an evaluation surface that is preferably within the model eye, and particularly preferably is still before the propagation of the object light from the eye lens (for example posterior lens surface or exit pupil) to the retina. In order to be able to implement the comparison, and therefore the evaluation of the wavefront of the object light, a corresponding reference wavefront is determined. The reference wavefront thereby describes a wavefront converging at a point on the retina of the personalized eye model.

In the event that the evaluation surface is provided at, for example, the posterior lens surface of the lens, in particular after the refraction at the posterior lens surface of the model eye, the resulting wavefront of the object light may preferably simply be compared with a spherical wavefront of the reference light. For this purpose, the method thus preferably includes a predetermination of a spherical wavefront striking the first surface of the spectacles lens; a determination of a wavefront in the at least one eye, said wavefront resulting from the spherical wavefront due to the effect of at least the first and second surface of the spectacles lens, the anterior corneal surface, and the lens of the model eye; and an evaluation of the aberration of the resulting wavefront in comparison to a spherical wavefront converging on the retina.

By contrast, in the event that an evaluation surface should be provided within the lens, or between the anterior corneal surface and the lens of the model eye, a reverse propagation from a point on the retina, through the individual components of the model eye, up to the evaluation surface is simply simulated as a reference light in order to produce a comparison of the object light with the reference light there.

However, as has already been mentioned above, a complete correction of the refraction of the eye for all viewing directions of the eye simultaneously, thus for all visual points of the at least one spectacles lens surface to be optimized, is generally not possible. A deliberately incorrect adaptation of the spectacles lens is thus preferably provided, depending on the viewing direction, which depending on the use situation is less in the primarily utilized regions of the spectacles lens (for example central visual points), somewhat greater in the less utilized regions (for example peripheral visual points). This procedure is already known in principle from conventional optimization methods.

In order to optimize the spectacles lens, the at least one surface of the spectacles lens that is to be calculated or optimized is now iteratively varied until an aberration of the resulting wavefront corresponds to a predetermined target aberration, thus in particular deviates by predetermined values of the aberration from the wavefront of the reference light (for example a spherical wavefront whose center of curvature lies on the retina). Here, the wavefront of the reference light is also referred to as a reference wavefront. For this purpose, the method preferably includes a minimization of an objective function F, in particular analogous to the objective function already described above, wherein—as is additionally described further below—higher-order aberrations are taken into account.

Within the scope of a preferred aspect of the present invention, for the calculation or optimization of a spectacles lens it has thus been proposed to establish such a personalized eye model which preferably is adapted in a personalized manner to the individual spectacles wearer, up to the retina. A numerical ray calculation and wavefront calculation is then performed at this personalized eye model such that this is preferably subdivided by the evaluation surface into two segments, of which a first segment includes a calculation of the object light, up to the personalized model eye or into the optimization model eye, for each visual point of the at least one surface of the spectacles lens that is to be calculated or optimized, whereas a second segment includes the determination of the reference wavefront corresponding to the personalized eye model. Both the calculation of the object light and the determination of the reference wavefront take place under consideration of higher-order aberrations of the respective wavefront and the refracting interfaces in the eye model. For this purpose, the eye model is populated, using the provided, in particular measured higher-order aberrations of the cornea of the eye of the spectacles wearer, with corresponding values of the individual parameters to describe the surface shapes (for example anterior lens surface and/or posterior lens surface), and if applicable under consideration of standard values for some of these parameters.

In particular a propagation of the object light, including HOAs, is therefore calculated for each visual point. The reference wavefront is also preferably emanating from the retina of the model eye (in backward propagation) up to the evaluation surface, likewise including HOAs. At the evaluation surface, the two wavefronts including HOAs are compared.

Within the scope of the present invention, it has turned out that the consideration of HOAs, in particular in an eye model, itself then leads to a distinct improvement of the personalized adaptation if the HOAs of the entire eye are not entirely measured in a personalized manner, but rather are derived in the eye model from personalized measurements only of the HOAs of the cornea (for example shape of the anterior corneal surface) and under standard assumptions for the HOAs of the eye and/or of the eye lens. It is therefore not necessary to measure the HOAs of the entire eye; rather, a very good personalized adaptation of the spectacles lens may already be achieved using the shape of the anterior corneal surface, which is less complicated to determine.

In particular, within the scope of the invention, the anterior corneal surface is measured in a personalized manner, and the eye lens of the personalized eye model is preferably calculated accordingly and/or at least partially established using standard values, in order to satisfy at least the personalized determined refraction data. In a preferred embodiment, the anterior conical surface (or its curvature) is thereby measured in a personalized manner along the principal sections (topometry). The establishment of the shape of the anterior corneal surface of the model eye using these measurements thereby takes place such that the aberrations of the cornea of the eye are thereby described, including the HOAs of the cornea. In a further preferred embodiment, the topography of the anterior corneal surface (meaning the complete description of the surface) is measured in a personalized manner. The establishment of the shape of the anterior corneal surface of the model eye using these measurements thereby takes place such that the aberrations of the cornea of the eye are thereby described, including the HOAs of the cornea.

In a further preferred embodiment, the establishment of the cornea-lens distance also takes place using personalized measured values for the cornea-lens distance.

The establishment of the parameters of the lens of the model eye particularly preferably includes an establishment of the following parameters:

a shape of the anterior lens surface, including of at least one higher-order aberration of the anterior lens surface;
    a lens thickness; and
    a shape of the posterior lens surface, including of at least one higher-order aberration of the posterior lens surface.

The establishment of the lens thickness and of the lens-retina distance preferably takes place using predetermined standard values. The method thereby preferably moreover includes a predetermination of standard values for higher-order aberrations (HOA) of the eye, as well as standard values for the shape of the posterior lens surface, including higher-order aberrations of the posterior lens surface. The shape of the anterior lens surface, including higher-order aberrations of the anterior lens surface, is preferably determined via calculation on the basis of these predetermined values and the provided, personalized refraction data of the eye and aberrations of the cornea and of the posterior lens surface.

In an alternative, preferred implementation, instead of the shape of the posterior lens surface (including HOAs), a shape of the anterior lens surface including HOAs of the anterior lens surface is predetermined as standard values. The shape of the posterior lens surface, including higher-order aberrations of the posterior lens surface, is preferably determined via calculation on the basis of the otherwise predetermined values and the provided, personalized refraction data of the eye and aberrations of the cornea and of the anterior lens surface.

In a further alternative, preferred implementation, the establishment of the lens thickness takes place using predetermined standard values, wherein the method moreover includes a predetermination of standard values for higher-order aberrations (HOA) of the eye. In particular, a vergence matrix $S_M$ including lower-order and higher-order aberrations is thus provided, wherein the lower-order aberrations correspond to the personalized refraction data of the eye, and the higher-order aberrations correspond to the predetermined standard values. Moreover, for at least one of the anterior lens surface and the posterior lens surface, the shape including higher-order aberrations is preferably inclusively provided using predetermined standard values. For the other lens surface, at least one parameter of a lower-order aberration, in particular a curvature in a normal section, is preferably provided in particular via personalized measurement. On the basis of these data, the lens-retina distance as well as the remaining parameters of the other lens surface are then determined via calculation.

In a further alternative, preferred implementation, the establishment of the lens thickness and of the lens-retina distance takes place using predetermined standard values. Moreover, the establishment of the shape of the anterior lens surface and of the posterior lens surface particularly preferably takes place using predetermined standard values for the higher-order aberrations of the respective surface. The HOAs are measured in a personalized manner only for the cornea of the eye of the spectacles wearer and are taken into account in the eye model. The standard values of the higher-order aberrations of the anterior lens surface and of the posterior lens surface are thereby particularly preferably set to zero.

In a preferred embodiment, the evaluation surface lies at the exit pupil of the model eye. The evaluation surface preferably lies at an interface of the model eye, in particular within the model eye, in particular at the posterior lens surface or at the anterior lens surface or at the cornea, or at a surface (interface) of the cornea (for example posterior corneal surface). The evaluation of the aberration of the wavefront propagating at the evaluation surface along the principal ray thereby particularly preferably includes a calculation of a refraction of the wavefront at the interface at which the evaluation surface is situated. The change of propagation steps and refraction steps in the numerical description and calculation of the path of the object light thus ends with a calculation step, whereas the subsequent propagation step already represents part of the simulation of the reference wavefront. It is precisely this procedure that has turned out to be particularly preferred. In particular, the calculation of the propagation of the wavefronts poses high requirements for numerical calculation units and requires a comparably large amount of processor time. Due to the termination of the calculation of the object light after a refraction, the subsequent light propagation does not need to be recalculated for each visual point and each iteration step. Instead, the same reference wavefront may be used for each iteration step, wherein a markedly good personalized adaptation of the spectacles lens is nevertheless achieved, at least insofar as the reference wavefront is preferably based on the personalized eye model.

In a further aspect, the invention relates to a device for determining personalized aberration data of at least one eye of a spectacles wearer, comprising:
- a data interface for providing a measured corneal topography of the at least one eye of the spectacles wearer (or a measurement device to measure the corneal topography of the at least one eye);
- a cornea evaluation module to determine personalized imaging properties of the cornea of the eye which describe at least higher-order aberrations of the cornea, $HOA_C$, from the measured corneal topography; and
- a calculation module to determine aberrations of the eye which describe at least higher-order aberrations of the eye, such that at least the higher-order aberrations of the eye, $HOA_{Eye}$, are determined under consideration of the determined personalized imaging properties of the cornea of the eye.

In a further aspect, the invention relates to a device for calculating or optimizing a spectacles lens for at least one eye of a spectacles wearer, comprising:
- a data interface for providing personalized aberration data which have been determined by means of a method according to the present invention, in particular in one of the preferred embodiments described here;
- a modeling module to determine a reference aberration at an evaluation surface using the provided personalized aberration data of the eye;
- a surface model database to predetermine a first surface and a second surface for the spectacles lens to be calculated or optimized;
- a primary ray determination module to determine the path of a primary ray through at least one visual point (i) of at least one surface of the spectacles lens, which surface is to be calculated or optimized;
- an evaluation module to evaluate an aberration of a wavefront at the evaluation surface, said wavefront resulting along the primary ray from a spherical wavefront striking the first surface of the spectacles lens, in comparison to the determined reference aberration; and
- an optimization module to iteratively vary the at least one surface of the spectacles lens, which surface is to be calculated or optimized, until the evaluated aberration corresponds to a predetermined target aberration.

Additional Aspects

Insofar as is not explicitly noted otherwise, aspects that are relevant to both the first approach and the second approach of the invention are described in the following paragraphs:

Moreover, the invention offers a method for producing a spectacles lens, including:
- calculation or optimization of a spectacles lens according to the method for calculation or optimization of a spectacles lens according to any of the present invention, in particular in a preferred embodiment; and
- manufacture of the spectacles lens so calculated or optimized.

Moreover, the invention offers a device for producing a spectacles lens, comprising:
- calculation or optimization means which are designed to calculate or optimize a spectacles lens according to the present invention, in particular in a preferred embodiment;
- machining means which are designed to machine the spectacles lens to completion.

Moreover, the invention offers a use of a spectacles lens produced according to the production method according to the present invention, in particular in a preferred embodiment, in a predetermined average or personalized usage position of the spectacles lens in front of the eyes of a defined spectacles wearer for correction of an ametropia of said spectacles wearer.

BRIEF DESCRIPTION OF THE FIGURE

Preferred embodiments of the invention are explained by way of example in the following, at least in part with reference to the accompanying drawing. Thereby shown is:

FIG. 1 a schematic depiction of the physiological and physical model of a spectacles lens and of an eye, together with a ray path, in a predetermined usage position.

DETAILED DESCRIPTION

First Approach

Insofar as is not explicitly noted otherwise, initial details regarding exemplary and preferred implementations of the first approach of the invention are described in the following paragraphs:

FIG. 1 shows a schematic depiction of the physiological and physical model of a spectacles lens and of an eye in a predetermined usage position, together with an exemplary ray path which forms the basis of a personalized spectacles lens calculation or optimization according to a preferred embodiment of the invention.

Preferably, only a single ray (the principal ray 10, which preferably travels through the eye's center of rotation Z') is hereby calculated per visual point of the spectacles lens, but moreover also accompanying the derivatives of the rises of the wavefront according to the transversal (orthogonal to the principal ray) coordinates. These derivatives are considered up to the desired order, wherein the second derivatives describe the local curvature properties of the wavefront, and the higher derivatives coincide with the higher-order aberrations.

Given the calculation of light through the spectacles lens, up to the eye 12, according to the personalized prepared eye model, the local derivatives of the wavefronts are determined in the end effect at a suitable position in the ray path in order to compare them there with a reference wavefront which converges at a point on the retina of the eye 12. In particular, the two wavefronts (meaning the wavefront coming from the spectacles lens and the reference wavefront) are compared with one another at an evaluation surface.

What is thereby meant by "position" is thereby not simply a defined value of the z-coordinate (in the light direction), but rather such a coordinate value in combination with the specification of all surfaces through which refraction has taken place before reaching the evaluation surface. In a preferred embodiment, refraction occurs through all refracting surfaces, including the posterior lens surface. In this instance, a spherical wavefront whose center of curvature lies on the retina of the eye 12 preferably serves as a reference wavefront.

Particularly preferably, as of this last refraction propagation does not continue, so that the radius of curvature of this reference wavefront corresponds directly to the distance between posterior lens surface and retina. In a moreover preferred embodiment, propagation does continue after the last refraction, and in fact preferably up to the exit pupil AP of the eye 12. For example, this is situated at a distance $d_{AR}=d_{LR}^{(b)}=d_{LR}-d_{LR}^{(a)}>d_{LR}$ in front of the retina, and therefore even in front of the posterior lens surface, so that in this instance the propagation is a back-propagation (the terms $d_{LR}^{(a)}$, $d_{LR}^{(b)}$ are described further below in the enumeration of steps 1-6). In this instance as well, the reference wavefront is spherical with center of curvature on the retina, but has curvature radius $1/d_{AR}$.

In this regard, it is assumed that a spherical wavefront $w_0$ emanates from the object point and propagates up to the first spectacles lens surface 14. There it is refracted and subsequently propagates up to the second spectacles lens surface 16, wherein it is refracted again. The wavefront $w_{g1}$ exiting from the spectacles lens subsequently propagates along the principal ray in the direction of the eye 12 (propagated wavefront $w_{g2}$) until it strikes the cornea 18, where it is again refracted (wavefront $w_c$). After a further propagation within the anterior chamber depth up to the eye lens 20, the wavefront is also refracted again by the eye lens 20, whereby the resulting wavefront $w_e$ is created at the posterior surface of the eye lens 20 or at the exit pupil of the eye, for example. This is compared with the spherical reference wavefront $w_s$, and for all visual points the deviations are evaluated in the objective function (preferably with corresponding weightings for the individual visual points).

The ametropia is thus no longer described only by a thin sphero-cylindrical lens, as this was typical in many conventional methods; rather, the corneal topography, the eye lens, the distances in the eye, and the deformation of the wavefront (including the lower-order aberrations—thus sphere, cylinder, and axis length—as well as preferably also including the higher-order aberrations) in the eye are preferably directly considered. In the eye model according to the invention, the vitreous body length $d_{LR}$ is thereby calculated in a personalized manner.

An aberrometer measurement preferably delivers the personalized wavefront deformations of the real, ametropic eye for far and near (deviations, no absolute refractive powers), and the personalized mesopic and photopic pupil diameters. A personalized real anterior corneal surface that generally makes up nearly 75% of the total refractive power of the eye is preferably obtained from a measurement of the corneal topography (areal measurement of the anterior corneal surface). In a preferred embodiment, it is not necessary to measure the posterior corneal surface. Due to the small refractive index difference relative to the aqueous humor, and due to the small cornea thickness, it is preferably described in good approximation not by a separate refractive surface, but rather by an adaptation of the refractive index of the cornea.

In general, in this specification bold-face lowercase letters designate vectors, and bold-face capital letters designate matrices, for example the (2×2) vergence matrices or refractive power matrices $$S = \begin{pmatrix} S_{xx} & S_{xy} \\ S_{xy} & S_{yy} \end{pmatrix},$$

$$C = \begin{pmatrix} C_{xx} & C_{xy} \\ C_{xy} & C_{yy} \end{pmatrix},$$

$$L = \begin{pmatrix} L_{xx} & L_{xy} \\ L_{xy} & L_{yy} \end{pmatrix},$$

$$1 = \begin{pmatrix} 1 & 0 \\ 0 & 1 \end{pmatrix},$$

and cursive letters such as d designate scalar values.

Furthermore, bold-face cursive capital letters should designate wavefronts or surfaces as a whole. For example, S is thus the vergence matrix of the identically named wavefront S; aside from the 2nd-order aberrations that are encompassed in S, S also includes the entirety of all higher-order aberrations (HOA) of the wavefront. Mathematically, S stands for the set of all parameters that are necessary in order to describe a wavefront (sufficiently precisely) with regard to a given coordinate system. S preferably stands for a set of Zernike coefficients having a pupil radius, or a set of coefficients of a Taylor series. S particularly preferably stands for the set from a vergence matrix S to describe the 2nd-order wavefront properties, and a set of Zernike coefficients (with a pupil radius) that serves to describe all remaining wavefront properties except for the 2nd order, or a set of coefficients according to a Taylor decomposition. Analogous statements apply to surfaces instead of wavefronts.

Among other things, the following data may in principle be measured directly:

the wavefront $S_M$ which is generated by the laser spot on the retina and the passage through the eye (from aberrometric measurement)

shape of the anterior corneal surface C (via corneal topography)

distance between cornea and anterior lens surface $d_{CL}$ (via pachymetry). This variable may also be determined indirectly via the measurement of the distance between the cornea and the iris; correction values may thereby be applied, if applicable. Such corrections may be the distance between the anterior lens surface and the iris, from known eye models (for example literature values).

curvature of the anterior lens surface in a direction $L_{1xx}$ (via pachymetry). Without limitation of the generality, the x-plane may thereby be defined such that this section lies in the x-plane. The coordinate system is thus defined so that this plane lies obliquely; the derivative must be expanded by the functions of the corresponding angle. It is not required that it thereby be a principal section. For example, it may be the section in the horizontal plane.

Furthermore—depending on the embodiment—the following data may either be measured or learned from the literature:

thickness of the lens $d_L$ curvature of the posterior lens surface in the same direction as the anterior lens surface $L_{2,xx}$ (via pachymetry)

Therefore, there are the following possibilities for the posterior lens surface:

measurement of $L_{2,xx}$ ($L_{2,M}$) and assumption of a rotational symmetry $L_{2,xx}=L_{2,yy}=L_2=L_{2,M}$ and $L_{2,xy}=L_{2,yx}=0$ taking $L_{2,xx}$ from the literature ($L_{2,Lit}$), and assumption of a rotational symmetry $L_{2,xx}=L_{2,yy}=L_2=L_{2,M}$ and $L_{2,xy}=L_{2,yx}=0$ taking the complete (asymmetrical) shape $L_2$ from the literature ($L_{2,Lit}$)

measurement of $L_{2,xx}$ ($L_{2,M}$), and assumption of a cylinder or an otherwise specified asymmetry $a_{Lit}$ from the literature $L_{2,xx}=L_{2,M}$ and $L_{2,xy}=L_{2,yx}=f(L_{2,xx},a_{Lit})$ as well as $L_{2,yy}=g(L_{2,xx},a_{Lit})$ The following data may be learned from the literature:

refractive indices $n_{CL}$ of cornea and anterior chamber depth, as well as of the aqueous humor $n_{LR}$ and that of the lens $n_L$ In particular, the distance $d_{LR}$ between posterior lens surface and retina, as well as the components $L_{1,yy}$ and $L_{1,xy}=L_{1,yx}$ of the anterior lens surface, therefore remain as unknown parameters. To simplify the formalism, the former may also be written as a vergence matrix $D_{LR}=D_{LR}\cdot 1$ with $D_{LR}=n_{LR}/d_{LR}$. Furthermore, the variable $\tau$ is generally used, which is defined as $\tau=d/n$ (wherein the corresponding index as is used for d and $\tau$ is always to be used for the refractive index as n, for example as $\tau_{LR}=d_{LR}/n_{LR}$, $\tau_{CL}=d_{CL}/n_{CL}$).

In a preferred embodiment in which the lens is described via an anterior surface and a posterior surface, the modeling of the passage of the wavefront through the eye model used according to the invention, thus after the passage through the surfaces of the spectacles lens, may be described as follows, wherein the transformations of the vergence matrices are explicitly indicated:

1. Refraction of the wavefront S with the vergence matrix S at the cornea C with the surface refractive power matrix C, relative to the wavefront $S'_C$ with vergence matrix $S'_C=S+C$
2. Propagation by the anterior chamber depth $d_{CL}$ (distance between cornea and anterior lens surface) relative to the wavefront $S_{L1}$ with vergence matrix $S_{L1}=S'_C/(1-\tau_{CL}\cdot S')$ $$S_{L1} = \frac{S'_C}{(1-\tau_{CL}\cdot S'_C)}$$

3. Refraction at the anterior lens surface $L_1$ with the surface refractive power matrix $L_1$ relative to the wavefront $S'_{L1}$ with the vergence matrix $S'_{L1}=S_{L1}+L_1$
4. Propagation by the lens thickness $d_L$ relative to the wavefront $S_{L2}$ with vergence matrix $S_{L2}=S'_{L1}/(1-\tau_L\cdot S'_{L1})$
5. Refraction at the posterior lens surface $L_2$ with the surface refractive power matrix $L_2$ relative to the wavefront $S'_{L2}$ with the vergence matrix $S'_{L2}=S_{L2}+L_2$
6. Propagation by the distance between lens and retina $d_{LR}$ relative to the wavefront $S_R$ with the vergence matrix $S_R=S'_{L2}/(1-\tau_{LR}\cdot S'_{L2})$ Each of the steps 2, 4, 6 in which propagation takes place over the distances $\tau_{CL}$, $\tau_{CL}$, or $\tau_{CL}$ may thereby be divided up into two partial propagations 2a,b), 4a,b), or 6a,b) according to the following scheme, which for step 6a,b) explicitly reads:

6a. Propagation by the distance $d_{LR}^{(a)}$ between lens and intermediate plane relative to the wavefront $S_{LR}$ with the vergence matrix $S_{LR}=S'_{L2}/(1-\tau_{LR}^{(a)}S'_{L2})$ 6b. Propagation by the distance $d_{LR}^{(b)}$ between intermediate plane and retina relative to the wavefront $S_R$ with the vergence matrix $S_R=S_{LR}/(1-\tau_{LR}^{(b)}S_{LR})$ $\tau_{LR}^{(a)}=d_{LR}^{(a)}/n_{LR}^{(a)}$ and $\tau_{LR}^{(b)}=d_{LR}^{(b)}/n_{LR}^{(b)}$ may thereby be positive or negative, wherein $n_{LR}^{(a)}=n_{LR}^{(b)}=n_{LR}$ and $\tau_{LR}^{(a)}+\tau_{LR}^{(b)}=\tau_{LR}$ should always be true. In each instance, step 6a and step 6b can be combined again via $S_R=S'_{L2}/(1-(\tau_{LR}^{(a)}+\tau_{LR}^{(b)})S'_{L2})=S'_{L2}/(1-\tau_{LR}S'_{L2})$. However, the division into step 6a and step 6b offers advantages, and the intermediate plane may preferably be placed in the plane of the exit pupil AP, which preferably is situated in front of the posterior lens surface. In this instance, $\tau_{LR}^{(a)}<0$ and $\tau_{LR}^{(b)}>0$.

The division of steps 2, 4 may also take place analogous to the division of step 6 into 6a,b).

For the selection of the evaluation surface of the wavefront, it is thus not only the absolute position in relation to the z-coordinate (in the light direction) but also the number of surfaces through which refraction has already taken place up to the evaluation surface. One and the same plane may thus be traversed repeatedly. For example, the plane of the AP (which normally is situated between the anterior lens surface and the posterior lens surface) is formally traversed by the light for the first time after a virtual step 4a, in which propagation takes place from the anterior lens surface by the length $\tau_L^{(a)}>0$. The same plane is reached for the second time after step 6a if, after refraction by the posterior lens surface, propagation takes place again back to the AP plane, meaning that $\tau_{LR}^{(a)}=-\tau_L+\tau_L^{(a)}=-\tau_L^{(b)}<0$, which is equivalent to $\tau_{LR}^{(a)}=\tau_{LR}-\tau_{LR}^{(b)}<0$. Given the wavefronts $S_{AP}$, which relate in the text to the AP, what should preferably always be meant (if not explicitly noted otherwise) is the wavefront $S_{AP}=S_{LR}$, which is the result of step 6a.

These steps 1 through 6 are referred to repeatedly in the further course of the specification. They describe a preferred correlation between the vergence matrix S of a wavefront S at the cornea and the vergence matrices of all intermediate wavefronts arising therefrom at the refractive intermediate surfaces of the eye, in particular the vergence matrix $S'_{L2}$ of a wavefront $S'_{L2}$ after the eye lens (or even of a wavefront $S_R$ at the retina). These correlations may be used both to calculate parameters (for example $d_{LR}$ or $L_1$) that are not known a priori, and thus to populate the model with values in either a personalized or generic manner, and in order to simulate the propagation of the wavefront in the eye with then populated models to optimize spectacles lenses.

In a preferred embodiment, the surfaces and wavefronts are treated up to the second order, for which a representation by vergence matrices is sufficient. Another preferred embodiment described still later takes into account and also utilizes higher orders of aberrations.

In a preferred embodiment, in a second-order description the eye model has twelve parameters as degrees of freedom of the model that need to be populated. These preferably include the three degrees of freedom of the surface refractive power matrix C of the cornea C; the respective three degrees of freedom of the surface refractive power matrices $L_1$ and $L_2$ for the anterior lens surface or posterior lens surface; and respectively one for the length parameters of anterior chamber depth $d_{CL}$, lens thickness $d_L$, and the vitreous body length $d_{LR}$.

Populations of these parameters may in principle take place in a plurality of ways:
  i) directly, thus personalized measurement of a parameter
  ii) a priori given value of a parameter, for example as a literature value or from an estimate, for example due to the presence of a measured value for another variable that correlates with the parameter to be determined in a known manner using a preceding population analysis
  iii) calculation from consistency conditions, for example compatibility with a known refraction The total number $df_2$ of second-order degrees of freedom of the eye model (df stands for "degree of freedom", the index "2" stands for 2nd-order) is thus composed of $$df_2 = df_2(i) + df_2(ii) + df_2(iii)$$

For example, if direct measured values are present for all twelve model parameters, then $df_2(i)=12$, $df_2(ii)=0$ and $df_2(iii)=0$, which for the sake of simplicity is expressed in the following by the notation $df_2=12+0+0$. In such an instance, the object refraction of the appertaining eye is also established, so that an objective refraction determination would no longer need to be additionally implemented.

However, a central aspect of the invention directly relates to the goal of not needing to directly measure all parameters. It is thus in particular markedly simpler to measure, or objectively and/or subjectively determine, the refraction of the appertaining eye than to measure all parameters of the model eye in a personalized manner. At least one refraction, thus measurement data regarding the wavefront $S_M$ of the eye up to the 2nd order that correspond to the data of the vergence matrix $S_M$, is thus preferably present. Given a population of the eye model purely on the basis of objectively measured data, these values may be taken from aberrometric measurements or autorefractometric measurements, or according to (ii) may be populated by data provided otherwise. A consideration of more subjective methods (i.e. subjective refraction), be it as a replacement for the objective measurement of the refraction or via the combination of both results, is further described later. The three conditions of the agreement with the three independent parameters of the vergence matrix $S_M$ therefore allow three parameters of the eye model to be derived, which in the notation introduced above corresponds to $df_2(iii)=3$.

In instances in which not all model parameters are accessible to direct measurements, or these measurements would be very costly, the invention thus utilizes the possibility of reasonably populating the missing parameters. For example, if direct measured values are present for at most nine model parameters ($df_2(i) \leq 9$), then the cited conditions of the refraction may be used in order to calculate three of the model parameters ($df_2(iii)=3$). In the event that $df_2(i)=9$ applies exactly, all twelve model parameters are then determined unambiguously via the measurements and the calculation, and ($df_2(ii)=0$) applies. By contrast, if $df_2(i)<9$, then $df_2(ii)=9-df_2(i)>0$, meaning that the model is underdetermined in the sense that $df_2(ii)$ parameters need to be established a priori.

With the provision of a personalized refraction, thus measurement data regarding the wavefront $S_M$ of the eye, in particular up to the second order, the necessary data of the vergence matrix $S_M$ are present. According to a conventional method described in WO 2013/104548 A1, in particular the parameters $\{C, d_{CL}, S_M\}$ are measured. By contrast, among other things the two length parameters $d_L$ and $d_{LR}$ (or $D_{LR}$) are conventionally established a priori (for example via literature values or estimation). In WO 2013/104548 A1, in particular a differentiation is made between the two instances in which either $L_2$ is established a priori and $L_L$ is calculated therefrom, or vice versa. The cited disclosure document discloses Equation (4) or Equation (5) as a calculation rule in this regard. For both instances, $df_2=4+5+3$ applies.

In the terminology of the aforementioned steps 1 through 6, the adaptation of $L_1$ to the measurements in particular occurs in that, on the one hand, the measured vergence matrix $S_M$ is calculated through the likewise measured matrix C by means of the steps 1, 2, and propagated up to the object-side side of the anterior lens surface. On the other hand, a spherical wave is calculated from back to front from an imaginary point light source on the retina by means of the steps 6, 5, 4, run through in reverse, in that this spherical wave is refracted at the previously established surface refractive power matrix $L_2$ of the posterior lens surface, and the wavefront that is then obtained propagates from the posterior lens surface up to the image-side side of the anterior lens surface. The difference of the vergence matrices $S_{L1}$ and $S'_{L1}$ that are determined in this manner, which difference must be present on the object side or image side of the anterior lens surface, must have been produced by the matrix $L_1$, because in the aberrometric measurement the measured wavefront arises from a wavefront that emanates from a point on the retina and therefore, due to the reversibility of the ray paths, is identical to that incident wavefront $(S=S_M)$ that converges on this point of the retina. This leads to Equation (4) in the cited disclosure document:

$$L_1(D_{LR}) = \frac{D_{LR} \cdot 1 - L_2}{1 + \tau_L \cdot (D_{LR} \cdot 1 - L_2)} - \frac{S_M + C}{1 - \tau_{CL}(S_M + C)} \quad (1a)$$

The other instance in the cited disclosure document relates to the adaptation of the matrix $L_2$ to the measurements after the matrix $L_1$ has been established. A difference now exists merely in that: the measured wavefront $S_M$ is subjected to the steps 1, 2, 3, 4, and the assumed wavefront from the point light source is only subjected to step 6; and in that the missing step that is to take place for adaptation of the posterior lens surface $L_2$ is now step 5, corresponding to Equation (5) of the cited disclosure document:

$$L_2 = D_{LR} - \left(\frac{S_M + C}{1 - \tau_{CL}(S_M + C)} + L_1\right)\left(1 - \tau_L\left(\frac{S_M + C}{1 - \tau_{CL}(S_M + C)} + L_1\right)\right)^{-1} \quad (1b)$$

The central idea of the invention is to calculate at least the length parameter $d_{LR}$ (or $D_{LR}$) from other measured data and a priori assumptions regarding other degrees of freedom, and not to assume it a priori as is conventional. Within the scope of the present invention, it has turned out that this therefore brought about a noteworthy improvement of the personalized adaptation at comparably low cost, because the wavefront calculation turned out to be very sensitively dependent on this length parameter. This means that, according to the invention, it is advantageous if at least the length parameter $d_{LR}$, which belongs to the $df_2(iii)=3$ parameters, that is calculated. This parameter is in particular poorly accessible to a direct measurement; it varies strongly between different test subjects, and these variations comparably strongly influence the imaging of the eye.

The data of the vergence matrix $S_M$, and particularly preferably also the data regarding C from personalized measurements, are preferably available. In a further preferred aspect that is preferably also taken into account in the following embodiments, a spherical posterior surface, meaning a posterior surface without astigmatic components, is assumed given an assumption of data regarding the posterior lens surface.

In a preferred embodiment of the invention, measurement data up to the second order that corresponding to the data of the surface refractive power matrix C are thus present with regard to the cornea C. Although these values may be learned from topographical measurements, the latter are not necessary. Rather, topometric measurements are sufficient. This situation corresponds to the instance $df_2=3+6+3$, wherein in particular the anterior chamber depth $d_u$, is one of the six parameters that are to be established a priori.

Insofar as no further personalized measurements are performed, a situation with $df_2=3+6+3$ is present. In order to be able to uniquely determine $d_{LR}$, six parameters from $\{L_1, L_2, d_L, d_{CL}\}$ must thus be populated via assumptions or literature values. The remaining two result from the calculation in addition to $d_{LR}$. In a preferred embodiment, the parameters of the posterior lens surface, the mean curvature of the anterior lens surface, and the two length parameters $d_L$ and $d_{CL}$ are populated a priori (as predetermined standard values).

In an instance that is particularly important to the invention, the anterior chamber depth $d_{CL}$ is thus additionally the distance between the cornea and the anterior lens surface, known for example from pachymetric or OCT measurements. The measured parameters therefore include $\{C, d_{CL}, S_M\}$. This situation corresponds to the instance of $df_2=4+5+3$. Afterward the problem is still mathematically underdetermined; five parameters must thus be established a priori from $\{L_1, L_2, d_L\}$ via assumptions or literature values. In a preferred embodiment, the parameters are the posterior lens surface, the mean curvature of the anterior lens surface, and the lens thickness. The precise way of calculating for this instance is presented in more detail further below.

Solely for the precision of the personalized adaptation, it is advantageous to be able to populate as many parameters as possible with personalized measurements. In a preferred embodiment, for this purpose the lens curvature is additionally provided in a normal section on the basis of a personalized measurement. A situation according to $df_2=5+4+3$ then thereby results, and it is sufficient to establish four parameters from $\{L_{1yy}, \alpha_{L1}, L_2, d_L\}$ a priori. Here as well, in a preferred embodiment these are again the parameters of posterior lens surface and the lens thickness. The precise calculation is again described in more detail further below.

In particular as an alternative to the normal step of the anterior lens surface, and particularly preferably in addition to the anterior chamber depth, the lens thickness may also be provided from a personalized measurement. The necessity to populate these parameters with model data or estimated parameters thereby disappears ($df_2=5+4+3$). Otherwise, the statements as already made above apply. This embodiment is particularly advantageous if a pachymeter is used whose measurement depth allows the detection of the posterior lens surface, but not a sufficiently certain determination of the lens curvatures.

In addition to the anterior chamber depth and a normal section of the anterior lens surface, in a preferred embodiment one additional parameter (for example measurement in two normal sections) or two additional parameters (measurement of both principal sections and the axis position) of the anterior lens surface are recorded via a personalized measurement. This additional information may in particular be utilized in two ways:

Abandonment of a priori assumptions: one or two of the assumptions that were otherwise made a priori may be abandoned and be determined via calculation. In this instance, the situations $df_2=6+3+3$ or $df_2=7+2+3$ result. In the first instance, the mean curvature of the posterior surface (given assumption of an astigmatism-free posterior surface) may be determined, and in the second instance the surface astigmatism (including axis position) may be determined for a given mean curvature. Alternatively, in both instances the lens thickness may be determined from the measurements.

However, such a procedure generally requires a certain caution, since noisy measurement data may easily lead to a "runaway" of the enabled parameters. The model may thereby as a whole become markedly worse instead of better. One possibility to prevent this is to predetermine anatomically reasonable limit values for these parameters, and to limit the variation of the parameters to this range. Of course, these limits may also be predetermined depending on the measured values.

Reduction of the measurement uncertainty: if, by contrast, the same a priori assumptions continue to be made (preferably thus $\{L_2, d_L\}$), the situations $df_2=6+4+3$ or $df_2=7+4+3$ are present; the system is thus mathematically overdetermined.

Instead of a simple analytical determination of $D_{LR}$ according to the subsequent embodiments, $D_{LR}$ (and possibly the still missing parameters from $L_1$) is determined ("fit") so that the distance between the $L_1$ resulting from the equations and the measured $L_1$ (or the measured $L_1$, supplemented by the missing parameters) is minimal. A reduction of the measurement uncertainty may—obviously—be achieved via this procedure.

In a further preferred implementation, the anterior chamber depth, two or three parameters of the anterior lens surface, and the lens thickness are measured in a personalized manner. The calculation of the remaining variables thereby takes place analogously, wherein the a priori assumption of the lens thickness may be replaced by the corresponding measurement.

In a further preferred implementation, personalized measurements of the anterior chamber depth, at least one parameter of the anterior lens surface, the lens thickness, and at least one parameter of the posterior lens surface are provided. This is hereby an expansion of the aforementioned instances. The respective additionally measured parameters may take place analogous to the step-by-step expansions of the above segments. These instances are particularly advantageous if the aforementioned pachymetry units that measure in one plane, two planes, or over the entire surface are accordingly extended in terms of measurement depth, and are so precise that the curvature data can be sufficiently precisely determined.

In the following it is shown, using a few examples, how the calculation of individual parameters may take place from the remaining measured parameters or parameters established a priori, and using the personalized refraction data.

For example, in preferred embodiments, a measurement of the curvature of a lens surface is available in a normal section. Since the posterior surface cannot be measured in practice without the anterior surface also being measured, and the measurement of the anterior surface preferably occurs, the equations for the instances of a curvature of the anterior lens surface that is known in a normal section are specified in the following. If, instead of a normal section of the anterior lens surface, a normal section of the posterior lens surface is present (for example corresponding measurements, model assumptions), one must analogously proceed with Equation (1b). Without limiting the generality, the coordinate system is placed so that the normal section travels in the x-direction. In a next step, the matrix equation (1a) is then evaluated in the given normal section and solved for $D_{LR}$, and this solution is subsequently used again in Equation (1a) for the complete specification of $L_1$.

If the xx-component of $L_1(D_{LR})$ from Equation (1) is set equal to the measured value $L_{1,xx}$, for this matrix element a quadratic equation in $D_{LR}$ is obtained whose positive solution corresponds to the distance between posterior lens surface and retina:

$$D_{LR} = \frac{-b + \sqrt{b^2 - 4c}}{2a} \quad (2)$$

It thereby applies that:

$a = \tau_L(1+\tau_L A)$ $b = 1 - \tau_L(tr(L_2) - AB)$ $c = A - L_{2,xx} + \tau_L \det L_2(1+\tau_L A) - \tau_L A \, tr(L_2) = A - L_{2,xx} + a \det L_2 - \tau_L A \, tr(L_2)$ (2a)

with $A = -S_{M,L1,xx} - L_{1,xx}$ $B = 2 - \tau tr(L_2)$ $\det(L_2) = L_{2,xx} L_{2,yy} - L_{2,xy}^2$ $tr(L_2) = L_{2,xx} + L_{2,yy}$ (2b)

and $$S_{M,L1,xx} = \frac{\tau_{CL} S''_{M,C,xy} + S'_{M,C,xx} \cdot (1 - \tau_{CL} S'_{M,C,yy})}{-\tau_{CL}^2 S'^2_{M,C,xy} + (1 - \tau_{CL} S'_{M,C,xx}) \cdot (1 - \tau_{CL} S'_{M,C,yy})} \quad (2c)$$

$S'_{M,C,xx} = S_{M,xx} + C_{xx}$ (xy und yy analog)

In the event of a symmetrical posterior lens surface ($L_2 = L_{2,xx} \cdot 1$), this simplifies to $$D_{LR} = L_{2,xx} + \frac{L_{1,xx} + S_{M,L1,xx}}{1 - \tau_L \cdot (L_{1,xx} + S_{M,L1,xx})} \quad (3)$$

with $S_{M,L1,xx}$ from Equation (2c).

In both instances, it is therefore possible to calculate the anterior lens surface $L_1$ in that the respectively obtained $D_{LR}$ in Equation (1a) is used:

$$L_1 = \frac{D_{LR} - L_2}{1 + \tau_L \cdot (D_{LR} - L_2)} - \frac{S_M + C}{1 - \tau_{CL}(S_M + C)} \quad (4)$$

The result is naturally symmetrical ($L_{1,xy} = L_{1,yx}$), and for the component $L_{1,xx}$ reproduces the value used in (2b) or (3).

In some preferred embodiments, a personalized measurement or a specification of a mean curvature of a lens surface is provided. For example, this situation is present when the mean curvature of the anterior lens surface may be measured, or no measurements at the lens surfaces may be performed and the mean curvature of a lens surface is assumed (for example taken from the literature). As was just now described, here the method for the anterior lens surface is described and can be analogously transferred to the posterior lens surface.

In this instance of a given mean sphere $L_{1,ms}$ of the anterior lens surface, the free parameters are the cylinder $L_{1,cyl}$ and the axis length $\alpha_{L1}$. With $L_{1,diff} = L_{1,cyl}/2$, $L_1$ becomes $$L_1 = \begin{pmatrix} L_{1,ms} - L_{1,diff} \cdot \cos 2\alpha_{L1} & -L_{1,diff} \cdot \sin 2\alpha_{L1} \\ -L_{1,diff} \cdot \sin 2\alpha_{L1} & L_{1,ms} + L_{1,diff} \cdot \cos 2\alpha_{L1} \end{pmatrix} \quad (5)$$

One again proceeds from Equation (1a). If the expressions for $L_1$ from Equations (5) and (1a) are now equated, an equation system is obtained that is made up of three equations (the two non-diagonal elements are identical) and the three unknowns $L_{1,diff}$, $\alpha_{L1}$ and $D_{LR}$. This has the physically relevant solution $$D_{LR} = \frac{-\bar{b} + \sqrt{\bar{b}^2 - 4\bar{a}\bar{c}}}{2\bar{a}} \quad (6)$$

$L_{1diff} = \pm\sqrt{\sigma^2 + \gamma^2}$ $\alpha_{L1} = \frac{1}{2}\arctan(\pm\gamma, \pm\sigma) + \frac{\pi}{2}$ with $\bar{a} = \tau_L(1 + \tau_L \bar{A})$ (6a)

$\bar{b} = 1 - \tau_L(tr(L_2) - \bar{A}B)$ $\bar{c} = \frac{1}{4}(\bar{A}B^2 - Btr(L_2) - \bar{a}Ast(L_2)^2)$ and $\bar{A} = \bar{S}_{M,L1} - \bar{L}_{1,meas}$ $Ast(L_2) = \sqrt{tr(L_2)^2 - 4\det L_2}$ $$\gamma = \frac{2(-1 + \sqrt{\bar{b}^2 - 4\bar{a}\bar{c}})(L_{2,xy} - L_{2,yy}) + \tau_L^2 Ast(L_2)^2(S_{M,L1,xx} - S_{M,L1,yy})}{2\tau_L^2 Ast(L_2)^2}$$

$$\sigma = \frac{2(-1 + \sqrt{\bar{b}^2 - 4\bar{a}\bar{c}})L_{2,xy} + \tau_L^2 Ast(L_2)^2 S_{M,L1,xy}}{2\tau_L^2 Ast(L_2)^2}$$

This can also be simplified for the instance of a rotationally symmetric posterior lens surface:

$$D_{LR} = L_2 + \frac{\bar{L}_{1,mess} + \bar{S}_{M,L1}}{1 - \tau_L \cdot (\bar{L}_{1,mess} + \bar{S}_{M,L1})} \quad (7)$$

-continued $$L_1 = (\overline{L}_{1,mess} + \overline{S}_{M,L1}) \cdot 1 - \frac{S_M + C}{1 - \tau_{CL}(S_M + C)}$$

wherein $$\overline{L}_{1,meas} = \frac{D_{LR} - L_2}{1 + \tau_L \cdot (D_{LR} - L_2)} - \overline{S}_{M,L1}$$

with $$\overline{S}_{M,L1} = \frac{S_{M,L1,xx} + S_{M,L1,yy}}{2}$$

The individual elements of the eye model can therefore be entirely calculated.

Aside from a principal section with given angle position, or the mean curvature, the given (i.e. measured or assumed) variables may also be other parameters such as the thickest principal section, the thinnest principal section, the cylinder, and the axis position. In these instances, the procedure is analogous to the illustrated instances.

Since the HOAs of the eye have also be now been taken into account in the optimization of spectacles lenses, it is advantageous to also consider the HOAs of the cornea or of the lens in the population of the eye model. Given the selection of HOAs for the lens, it generally applies that HOAs that may also represent the refractive index curve within the lens may be associated with the anterior lens surface or posterior lens surface.

The previously depicted formalism is preferably expanded, in particular with regard to the cited steps 1 through 6, to the co-treatment of the HOAs, in that the calculation methods from the publications by G. Esser et al.: "Derivation of the refraction equations for higher order aberrations of local wavefronts at oblique incidence", JOSA A, Vol. 27, No. 2 (2010), and by G. Esser et al.: "Derivation of the propagation equations for higher order aberrations of local wavefronts", JOSA A, Vol. 28, No. 11 (2011), are applied aside from the formulas for the vergence matrices that are explicitly specified in steps 1 through 6.

In general, the procedure with regard to the enumeration of degrees of freedom is executed in a manner very similar to as above. If, aside from data regarding 2nd-order errors, data about their HOAs are present (either from measurements or from reasonable assumptions) with regard to refractive surface C of the cornea and regarding the outgoing wavefront $S_M$, the wavefront $S_{L1}$ may also be determined computationally with accordingly many HOAs. This applies independently of the form in which the HOA presents itself. However, the Taylor series is particularly preferred, because in this form the statement exactly applies: if HOA coefficients up to the n-th order are present with regard to two surfaces C and $S_M$, the corresponding HOA coefficients for $S_{L1}$ can then also be computationally determined therefrom up to the n-th order. Furthermore, the Zernike basis is preferred, because here as well a similar statement applies. However, this is exact only when all Zernike coefficients with an order >n vanish.

An order n is preferably established (in advance), up to which all participating surfaces and wavefronts should be treated. Independently of the presentation of the HOAs, aside from the three components for the 2nd-order errors, the wavefronts or surfaces then additionally possess N components for the HOAs, wherein N depends on n and, inter alia, on the presentation form of the HOAs (in the Taylor decomposition and Zernike decomposition, N=(n+1)(n+2)/2-6 applies).

The adaptation condition using a measured wavefront, for example $S_{M,L1}$, then accordingly no longer possesses only the three components described above, but rather a maximum of N+3 components in total. These are then accordingly accompanied by 3 (N+3)+3=3N+12 parameters (namely the three length parameters $d_{CL}$, $d_L$ and $d_{LR}$ (or $D_{LR}$), as well as respectively N+3 components of the cornea C and the lens surfaces $L_1$ and $L_2$). This means that $$df_n = df_n(i) + df_n(ii) + df_n(iii)$$
$$= 3N + 12$$

applies, with $df_n(iii)$=N+3. If the anterior chamber depth $d_{CL}$ and the cornea C are preferably measured again, $df_n(i)$=N+4 applies, and consequently $df_n(ii)$=N+5, corresponding to the situation of $df_n$=(N+4)+(N+5)+(N+3).

The further procedure may be implemented in a manner very analogous to as described above.

Given the measurement device forming the basis of the procedure described here, the HOAs of the mapping of the eye on the retina may be detected in transmission with the aberrometry unit. The HOAs of the cornea surface may also be measured in reflection with the same device, via the topography unit. Both the exiting wavefront $S_M$ and the refractive surface C of the cornea, including the HOAs up to a defined order n, are therefore available. The wavefront $S_M$ supplies $df_n(iii)$=N+3 conditions for parameter calculation. Aside from the cornea C, if it is again preferred to also measure the anterior chamber depth $d_{CL}$, $df_n(i)$=N+4 applies, and consequently $df_n(ii)$=N+5, corresponding to the situation of $df_n$=(N+4)+(N+5)+(N+3).

In a preferred embodiment of the invention, in the population of the model the HOAs of the lens may now be selected so that, given the propagation of a wavefront emanating from a point on the retina according to steps 1 through 6, the measured wavefront arises in the reverse order.

According to the invention, however, it is proposed that at least the length parameter $d_{LR}$ is measured neither a priori nor in a personalized manner, but rather is calculated using the personalized refraction data and the data otherwise established (in advance). For this purpose, at least one measured value or an assumption is provided in particular for one of the degrees of freedom of lens surfaces $L_1$ or $L_2$. for example, if this is a measured value for the curvature of $L_1$ in a normal section, then $d_{LR}$ (or $D_{LR}$) may be determined therefrom via calculation.

If the specification in the vergence matrices relates to the local curvature (this corresponds to the specification of the HOAs as coefficients of a Taylor decomposition), for this purpose $D_{LR}$ and the missing parameters of the lens are first determined as has already been described above. Following this, the HOAs of the lens may be constructed step by step, starting from the second order to n-th order, with the formalism from G. Esser et al.: "Derivation of the refraction equations for higher order aberrations of local wavefronts at oblique incidence", JOSA A, Vol. 27, No. 2 (2010), and from G. Esser et al.: "Derivation of the propagation equations for higher order aberrations of local wavefronts", JOSA A, Vol. 28, No. 11 (2011).

By contrast, if the mean curvature over a defined pupil is used—which is the case in the presentation according to Zernike, for example—the degree of freedom $D_{LR}$ is likewise established. In this formalism, an iterative procedure would be necessary due to the dependencies. However, this can be avoided via a conversion between the two notations before the beginning of the calculation.

Even if neither a topograph nor an aberrometer is used, thus even if no personalized measurement data regarding HOAs are present, model-based assumptions about the HOAs of the cornea, the lens, or the eye may nevertheless be made and be used in the population of the eye model. The assumed values may thereby also be selected using corresponding models depending on measured data (for example with refraction values, results of the topometry or autorefractometer measurement). Examples for the precise calculation have already been described further above, wherein the corresponding assumptions occur instead of the measured values for the HOAs. This also applies again in particular to spherical aberrations, and since this is markedly different than zero, averaged across the population. This may thereby be chosen independently of the measured data, or depending on measured data (for example refraction values, results of the topometry or autorefractometer measurement) and be associated with the cornea, one of the two lens surfaces, or combinations.

Due to the great importance of subjective refraction, it is advantageous that the results of such a subjective eyeglass determination can at least partially enter into the population of the model for the optimization. Subjective refraction data are preferably provided in the form of sphere, cylinder, and axis position. For the sake of simplicity, the description of the procedure is orientated toward this notation, with sph, cyl, and $\alpha$ for the values of sphere, cylinder, and axis position.

If HOAs are not considered, the process may continue as follows:

If only the values of the subjective refraction enter into the optimization, the measurement of the wavefront $S_M$ by an aberrometer or an autorefractometer may be omitted, and instead the matrix $S_M$ may be constructed from the subjective values:

$$S_M = \begin{pmatrix} \left(sph + \frac{1}{2} \cdot cyl\right) - \frac{1}{2} \cdot cyl \cdot \cos(2a) & -\frac{1}{2} \cdot cyl \cdot \sin(2a) \\ -\frac{1}{2} \cdot cyl \cdot \sin(2a) & \left(sph + \frac{1}{2} \cdot cyl\right) + \frac{1}{2} \cdot cyl \cdot \cos(2a) \end{pmatrix}$$

However, the results of the subjective refraction are preferably combined with those of the aberrometric or autorefractometric measurement. For this purpose, an optimized refraction is determined on the basis of both data sets, for example according to a method described in DE 10 2007 032 564 A1. This is described by the values $sph_{opt}$, $cyl_{opt}$ and $a_{opt}$. Analogous to the preceding section, $S_M$ is obtained as $$S_M = \begin{pmatrix} \left(sph_{opt} + \frac{1}{2} \cdot cyl_{opt}\right) - \frac{1}{2} \cdot cyl_{opt} \cdot \cos(2a_{opt}) & -\frac{1}{2} \cdot cyl_{opt} \cdot \sin(2a_{opt}) \\ -\frac{1}{2} \cdot cyl_{opt} \cdot \sin(2a_{opt}) & \left(sph_{opt} + \frac{1}{2} \cdot cyl_{opt}\right) + \frac{1}{2} \cdot cyl_{opt} \cdot \cos(2a_{opt}) \end{pmatrix}$$

According to DE 10 2007 032 564 A1, not all values of the subjective refraction or objective measurement need to enter into the optimized refraction values. For example, in the event of a determination of the optimized refraction values for near, or in the event of anticipated instrument myopia, the use of the objectively measured sphere or of the objectively measured defocus term may be omitted.

Even given the incorporation of subjective refraction data, the HOAs may also be taken into account again in the population of the model. For this purpose, given use of the subjective refraction values it is necessary to have these enter into the data set in a consistent manner. To simplify the presentation, in the following a formalism is chosen on the basis of Zernike coefficients, wherein in principle a different basis may also be used.

In the following, the correlation between a set of Zernike coefficients for representation of the wavefronts ($c_{nm}$), with $r_0$ as a radius of the wavefront, and refraction values (sph, cyl, a), is initially considered. The radius $r_0$ is preferably either measured or is established on the basis of model assumptions. Given use of the RMS metric, for example, the bijective correlation results as $$\begin{pmatrix} c_{2,-2} \\ c_{2,0} \\ c_{2,+2} \end{pmatrix} = g_{RMS}(sph, cyl, a) = \frac{r_0^2}{2\sqrt{6}} \begin{pmatrix} \frac{1}{2} \cdot cyl \cdot \sin(2a) \\ -\frac{1}{\sqrt{2}} \cdot \left(sph + \frac{1}{2} cyl\right) \\ \frac{1}{2} \cdot cyl \cdot \cos(2a) \end{pmatrix} \Leftrightarrow \begin{pmatrix} sph \\ cyl \\ a \end{pmatrix} =$$

$$f_{RMS}(c_{2,-2}, c_{2,0}, c_{2,+2}) = \begin{pmatrix} -\frac{4\sqrt{3}}{r_0^2} \cdot \left(c_{2,0} - \frac{1}{\sqrt{2}} \cdot \sqrt{c_{2,-2}^2 + c_{2,+2}^2}\right) \\ -\frac{4\sqrt{6}}{r_0^2} \cdot \sqrt{c_{2,-2}^2 + c_{2,+2}^2} \\ \frac{1}{2} \cdot \arctan(c_{2,+2}, c_{2,-2}) + \frac{\pi}{2} \end{pmatrix}$$

However, this is to be understood only as an example of a metric of the general form $$\begin{pmatrix} sph \\ cyl \\ a \end{pmatrix} = f_0(c_{2,-2}, c_{2,0}, c_{2,+2}) \Leftrightarrow \begin{pmatrix} c_{2,-2} \\ c_{2,0} \\ c_{2,+2} \end{pmatrix} = g_0(sph, cyl, a). \qquad (8)$$

Moreover, there are correlations in which HOAs also enter into the refraction values. This mapping is then always surjective for the calculation of the refraction values, but no longer bijective, meaning that the complete set of all Zernike coefficients of all mapping errors cannot be unambiguously reproduced from the refraction values. However, the coefficients of the lower-order mapping errors can also be unambiguously determined here again if the coefficients for the HOAs are predetermined:

$$\begin{pmatrix} sph \\ cyl \\ a \end{pmatrix} = f_1(c_{2,-2}, c_{2,0}, c_{2,+2}, c_{i,j}) \Leftrightarrow \begin{pmatrix} c_{2,-2} \\ c_{2,0} \\ c_{2,+2} \end{pmatrix} = g_1(sph, cyl, a, c_{i,j})(i > 2) \quad (9)$$

Naturally, analogous calculations and derivation are also possible in other notations, for example with the local derivatives of the wavefronts that are used in the publications by G. Esser et al.: "Derivation of the refraction equations for higher order aberrations of local wavefronts at oblique incidence", JOSA A, Vol. 27, No. 2 (2010), and by G. Esser et al.: "Derivation of the propagation equations for higher order aberrations of local wavefronts", JOSA A, Vol. 28, No. 11 (2011). If autorefractometric measurement with data regarding HOAs are present, these data or portions of these data may be used, together with the subjective refraction values, in order to determine a set of optimized refraction data, for example according to DE 10 2007 032 564 A1. The simultaneous use of both subjective refraction data and of the measured data is thereby not necessary. The variables, which in this section are referred to in the following as optimized refraction values (sph$_{opt}$, cyl$_{opt}$ and a$_{opt}$), may thus also be directly adopted from the subjective refraction determination without the use of objective measurement variables.

In principle, not all values of the subjective refraction or of the objective measurement need to enter into the optimized refraction values. For example, in the event of a determination of the optimized refraction values for near, or in the event of anticipated instrument myopia, the use of the objectively measured sphere or of the objectively measured defocus term may be omitted.

A wavefront (preferably represented by the Zernike coefficients $o_{i,j}$) that corresponds to these optimized values is then determined on the basis of the optimized refraction values. This wavefront is then used instead of the measured exiting wavefront described above. Given use of a metric according to Equation (8), the 2nd-order coefficients of this wavefront may be calculated according to Equation (8) from the optimized refraction values, and the higher-order coefficients may be directly adopted from the objective measurement of the exiting wavefront represented by the coefficient $m_{i,j}$:

$$\begin{pmatrix} o_{2,-2} \\ o_{2,0} \\ o_{2,+2} \end{pmatrix} = g_0(sph_{opt}, cyl_{opt}, a_{opt})$$

$$o_{i,j} = m_{i,j}(i > 2)$$

By contrast, given use of a metric according to Equation (9), the second-order coefficients of the wavefront ($o_{i,j}$) are not only dependent on the optimized refraction, but rather are by contrast to be chosen so that $$\begin{pmatrix} sph_{opt} \\ cyl_{opt} \\ a_{opt} \end{pmatrix} = f_1(o_{2,-2}, o_{2,0}, o_{2,+2}, c_{i,j})(i > 2)$$

applies, and therefore additionally directly depend on the higher-order coefficients of the measured exiting wavefront ($m_{i,j}$):

$$\begin{pmatrix} o_{2,-2} \\ o_{2,0} \\ o_{2,+2} \end{pmatrix} = g_1(sph_{opt}, cyl_{opt}, a_{opt}, m_{i,j})o_{ij} = m_{ij}$$

The evaluation of the aberrations during the calculation or optimization method may be performed at different locations in the ray path, meaning that the evaluation surface may be provided at different positions. Instead of taking place at the retina or at the posterior lens surface, an evaluation of the imaging wavefront may also already take place at a surface that is situated further forward in the model eye. For this purpose, within the model eye a reference wavefront R is defined that is then used in the lens optimization, for example. This reference wavefront thereby has the property that, given further propagation through the eye up to the retina, it leads to a point image. The reference wavefront may accordingly be determined, via back-propagation of a wavefront that converges at a point on the retina, from the retina up to the position of the reference wavefront. Since the measured wavefront $S_M$ is precisely the wavefront that emanates from a point light source on the retina, this may instead also be propagated inside the eye up to the position of the reference wavefront.

Considered mathematically, both procedures are equivalent and lead to the same formulas for the reference wavefront. In the following, to derive the corresponding reference wavefronts the path is respectively chosen that manages with fewer propagation steps and enables a simpler representation. In the following, for example, only the treatment of the components of the defocus and astigmatism is described. However, an expansion to HOAs and the use of subjective refraction is likewise possible and advantageous.

Given the consideration of HOAs, these may take place analogous to the calculation of the HOAs according to the embodiments in the following, via refraction (G. Esser et al.: "Derivation of the refraction equations for higher order aberrations of local wavefronts at oblique incidence", JOSA A, Vol. 27, No. 2 (2010)) and propagation (G. Esser et al.: "Derivation of the propagation equations for higher order aberrations of local wavefronts", JOSA A, Vol. 28, No. 11 (2011)).

Since the wavefront propagation is a non-linear process, a spectacles lens optimization that evaluates an imaging wavefront via comparison with a reference wavefront generally leads to different results depending on at which surface within the eye this comparison occurs.

In a preferred embodiment, only the ultimate step (in particular step 6b) is omitted, thus the propagation from the AP to the retina. The incident wavefront is thus only simulated up to the AP after the refraction at the posterior lens surface (thus calculation of $S_{AP}$ according to the aforementioned step 6a), and there is compared with a reference wavefront $R_{AP}$. This is thereby characterized in that in that, given the propagation to the retina, a point image results there. According to the above statement, the vergence matrix of this wavefront is precisely $$R_{AP} = D_{AP} = D_{LR}^{(b)} = \frac{1}{\tau_{LR}^{(b)}} 1 = \frac{1}{\tau_{LR} - \tau_{LR}^{(a)}} 1 = \frac{1}{1/D_{LR} - d_{LR}^{(a)}/n_{LR}} 1$$

with the $D_{LR}$ determined from Equation (2) or (3), as well as the negative (accommodation-dependent) value $d_{LR}^{(a)}<0$, whose absolute value describes the distance between the posterior lens surface and the AP.

In a furthermore preferred embodiment, the penultimate step, thus the propagation from the posterior lens surface to the retina as a whole, is moreover omitted. The incident wavefront is thus simulated only up to after the refraction at the posterior lens surface (thus calculation of $S'_{L2}$ according to the aforementioned step 5), and there is compared with a reference wavefront $R'_{L2}$. This is thereby characterized in that, given the propagation to the retina, it yields a point image there. According to the above statement, the vergence matrix of this wavefront is precisely $$R'_{L2}=D'_{L2}=D_{LR}\cdot 1$$

with the $D_{LR}$ determined from Equation (2) or (3).

A further simplification results if the comparison is placed before the refraction by the posterior lens surface. In this instance, the incident wavefront must be simulated, thus calculated, only up to $S_{L2}$ according to the above step 4. For this purpose, analogous to $S'_{L2}$, a reference wavefront $R_{L2}$ is defined that, after the refraction at the posterior lens surface and the propagation to the retina, yields a point image there. This is determined as $$R_{L2}=R'_{L2}-L_2=D_{LR}\cdot 1-L_2$$

with the $D_{LR}$ determined from Equation (2) or (3) and the $L_2$ known from the literature or from measurements.

In the event of a rotationally symmetrical posterior lens surface, this simplifies to $$R_{L2}=(D_{LR}-L_{2,xx})\cdot 1$$

In particular insofar as the lens thickness is likewise taken from the literature, in a further preferred embodiment it is suggested to omit the propagation through the lens as a next step, and to execute the comparison after the refraction by the anterior lens surface. In continuation of the above statement, for this purpose a reference wavefront $R'_{L1}$ is preferably used that arises from $R_{L2}$ via backward propagation by the lens thickness and has the following vergence matrix:

$$R'_{L1}=R_{L2}/(1+\tau_L R_{L2})$$

with the $D_{LR}$ determined from Equation (2) or (3), and the $\tau_L=d_L/n_L$ known from the literature or from measurements, as well as the vergence matrix $R_{L2}$ determined from Equation (6) or (7).

In the event of a rotationally symmetrical posterior lens surface, this simplifies to $$R'_{L1}=\frac{D_{LR}-L_{2,xx}}{1+\tau_L\cdot(D_{LR}-L_{2,xx})}\cdot 1$$

As given the above model, here it also applies that, even if the consideration occurs before the last steps and— depending on notation—the variable $D_{LR}$ does not explicitly appear, this variable nevertheless at least implicitly appears together with $d_L$ and $L_2$, since they together control the distribution of the effect $L_1$ in the anterior lens surface.

Yet another simplifications results if the comparison is placed before the refraction by the anterior lens surface. In this instance, the incident wavefront only needs to be simulated up to $S_{L1}$ according to step 2. For this purpose, analogous to $R'_{L1}$ a reference wavefront $R_{L1}$ is defined that, after the refraction at the anterior lens surface and the further steps, converges to a point on the retina. This may be calculated either via the refraction of $R'_{L1}$ at $L_1$, or be determined directly from the refraction of the measured wavefront $S_M$ at the cornea C and a subsequent propagation by $d_{CL}$. In both instances, one obtains $$R_{L1}=\frac{S_M+C}{1-\tau_{CL}\cdot(S_M+C)}$$

The variables $D_{LR}$, $d_L$ and $L_2$ no longer enter therein; it is thus sufficient to know $S_M$, C and $d_{CL}$.

One embodiment, in which the comparison is performed after the refraction at the cornea, is linked with relatively little computational cost. In this instance, only $S_M$ and C are still considered:

$$R'_C=S_M+C$$

An additional, very efficient possibility is the positioning of the evaluation surface at the exit pupil of the model eye. This preferably lies before the posterior lens surface.

The eye model and the population of the same may be expanded as follows:

In principle, the eye model may differ between cornea and anterior chamber. For this purpose, a posterior corneal surface $C_2$ is introduced at a distance $d_C$ after the anterior corneal surface anterior surface $C_1$ (formerly C), and two different refraction indices $n_C$ or $n_{CL}$ are specified for cornea and anterior chamber. The first step stated above (refraction of the wavefront S at the cornea C into wavefront $S'_C$ with vergence matrix $S'_C=S+C$) is also replaced by the following three steps:

1a: refraction of the wavefront S at the anterior corneal surface $C_1$ into wavefront $S'_{C1}$ with the vergence matrix $S'C_1=S+C_1$ 1b: propagation by the thickness of the cornea $d_C$ to the wavefront $S_{C2}$ with the vergence matrix $S_{C2}=S'_{C1}/(1-\tau_C S'_{C1})$ 1c: refraction at the posterior corneal surface $C_2$ into wavefront $S'_{C2}$ with the vergence matrix $S'C_2=S_{C2}+C_2$ wherein $$\tau_c=\frac{d_c}{n_c}.$$

Analogous to the other values, here the values for $d_C$ and $C_2$ may also be respectively measured, taken from the literature, or derived. As an example, a few possibilities for $C_2$ are described here:

In the event that no measurement at the posterior corneal surface is present, the shape of the posterior corneal surface may be taken from known eye models. Alternatively, in this instance the posterior corneal surface may also be derived from the measured shape of the anterior corneal surface. For this purpose, it is suggested to assume either a uniform corneal thickness (defined, for example, as emanating "in the direction of the rise" or "in a radial direction from a 'center of corneal curvature'"). The thickness may thereby either be learned from a measurement, be derived from this, or be learned from the literature. Furthermore, local properties may also be transferred only in part to the posterior surface.

If only a principal section of the posterior corneal surface is measured, this information may be used in order to reconstruct the entire posterior surface. For example, this may occur via the preparation of a function of the thickness or rise of the posterior corneal surface from the radius or the thickness of the rise of the anterior surface.

In most such instances, the anterior and posterior corneal surfaces are thereby known in the same normal section (meaning here in the x-direction).

The fact that the human eye is a non-centered optical system may thereby allow that the optical elements are arranged offset and/or tilted relative to a central axis.

This may relate to the individual elements as a whole (i.e. cornea and lens), or to all refractive surfaces individually (anterior corneal surface, possibly posterior corneal surface, anterior lens surface, and posterior lens surface). The corresponding parameters are respectively, for example, two lateral coordinates of the displacement of the center of the element or of the surface from the central axis, and two tilt angles. Alternatively, first-order Zernike coefficients (tip/tilt) may also be used.

The relevant variable that is affected by the change with regard to a centered system is the principal ray that forms the basis of the invention for all calculations, and which corresponds to the centered systems of the optical axis that have been dealt with up to now. In the general instance, the principal ray is that ray that emanates from the retina as a center of the measurement wavefront (preferably the site of the fovea) and passes through the middle of the entrance pupil. What is different than in the centered system, in which this ray coincides at suitable coordinates with the global z-axis of the eye model, is that the ray is now straight only in segments, from interface to interface, and also strikes off-center and at defined angles of incidence at each interface. The path of the principal ray, the positions of the penetration points, and the respective angles of incidence must be determined before calculation of the wavefronts (in the second order or higher order).

If the changes of the individual elements relative to a centered system are small, the principal ray may be approximately determined via the following affine equations. These correspond to an affine, expanded form of the linear optics in relation to a global coordinate system. Each propagation of a ray with lateral coordinate r and direction angle $\alpha$ relative to the global z-axis by a length d is thereby mapped, via the 2×2 transfer matrix equation $$\begin{pmatrix} r' \\ \alpha' \end{pmatrix} = \begin{pmatrix} 1 & d \\ 0 & 1 \end{pmatrix} \begin{pmatrix} r \\ \alpha \end{pmatrix}, \tag{10a}$$

to the propagated ray with lateral coordinate r' and direction angle $\alpha'$. By contrast, the refraction is described by the expanded 2×2 transfer matrix equation $$\begin{pmatrix} r' \\ \alpha' \end{pmatrix} = \begin{pmatrix} 1 & 0 \\ (\frac{n}{n'}-1)\rho & \frac{n}{n'} \end{pmatrix} \begin{pmatrix} r \\ \alpha \end{pmatrix} + \begin{pmatrix} \Delta r \\ \Delta \alpha \end{pmatrix}. \tag{10b}$$

$\rho$ is thereby the curvature of the refractive surface, and n, n' are the refraction indices before and after the refraction. $\Delta r$ and $\Delta \alpha$ are additionally correction portions of the ray parameters that materialize due to the lateral displacement and the tilting of the refractive interface, and may be determined from the tilt parameters and displacement parameters of the surface, for instance with Prentice's Rule. In the event of cylindrical surfaces, the 4×4 transfer matrix equations are to be used accordingly.

If the approximation described in Equations (10a) and (10b) is not sufficient, the principal ray, meaning all penetration points through the surfaces, may be numerically determined. In both instances, the principal ray determination has the effect that all propagation distances, the coordinates of the penetration points, and the angles of incidence and emergence, $\varepsilon$, $\varepsilon'$ are determined at each interface. In the event of the affine equations, $\varepsilon$, $\varepsilon'$ result from $\alpha$, $\alpha'$, and the surface normals that can be determined from r, the decentration, and the dioptric effect according to Prentice's Rule at the penetration point. In the general instance, $\varepsilon$, $\varepsilon'$ result from the numerical principal ray calculation and the surface normals at the penetration point r. The latter may be calculated instead of the penetration point r, for example via derivation of the surface representation (for example Taylor representation or Zernike representation around the point r=0, or B-splines).

In the event of the affine equations, the surface refractive power matrix C is constant and given by the respective refractive element. In the event of numerical calculation, C results at the penetration point via the local second derivatives in relation to a local coordinate system.

With the angles of incidence and emergence $\varepsilon$, $\varepsilon'$ that are calculated in such a manner, and possibly the newly determined surface refractive power matrix C, the calculation methods of the invention as described in the following may also be applied to decentered systems:

In the second order, instead of the vergence equation in matrix form S'$_C$=S+C, the generalized Coddington equation occurs $$\text{Cos}(\varepsilon') S'_C \text{Cos}(\varepsilon') = \text{Cos}(\varepsilon) S \text{Cos}(\varepsilon) + vC \tag{11}$$

with $$v = \frac{n'\cos\varepsilon' - n\cos\varepsilon}{n' - n} \tag{11a}$$

$$\text{Cos}(\varepsilon) = \begin{pmatrix} 1 & 0 \\ 0 & \cos(\varepsilon) \end{pmatrix} \text{ und } \text{Cos}(\varepsilon') = \begin{pmatrix} 1 & 0 \\ 0 & \cos(\varepsilon') \end{pmatrix}$$

Instead of the propagation equation S'=S/(1−$\tau$S) with $\tau$=d/n, the matrix equation $$S' = S/(1 - \tau_{\alpha,r} \cdot S) \text{ mit } \tau_{\alpha,r} = d_{\alpha,r}/n \tag{12}$$

occurs. $d_{\alpha,r}$ thereby designates the actual spatial distance between the penetration point of the successive surfaces.

If HOAs should be considered as well, instead of Equations (11) and (12), for refraction and propagation the corresponding expanded equations for the respective orders are to be used from publications by G. Esser et al.: "Derivation of the refraction equations for higher order aberrations of local wavefronts at oblique incidence", JOSA A, Vol. 27, No. 2 (2010), and by G. Esser et al.: "Derivation of the propagation equations for higher order aberrations of local wavefronts", JOSA A, Vol. 28, No. 11 (2011), and for this purpose the coefficients of the Taylor expansion of the refractive surface are to be determined as described (ibid.) in the coordinate system of the ray incidence.

Furthermore, a diaphragm—likewise also displaced or tilted—may be introduced in order to take into account the vignetting by the iris.

Second Approach

Insofar as is not explicitly noted otherwise, details regarding exemplary and preferred implementations of the second approach of the invention are now described in the following paragraphs:

FIG. 1 shows a schematic depiction of the physiological and physical model of a spectacles lens and of an eye in a predetermined usage position, together with an exemplary ray path which forms the basis of a personalized spectacles lens calculation or optimization according to a preferred embodiment of the invention.

Preferably, only a single ray (the principal ray 10, which preferably travels through the eye's center of rotation Z') is hereby calculated per visual point of the spectacles lens, but moreover also accompanying the derivatives of the rises of the wavefront according to the transversal (orthogonal to the principal ray) coordinates. These derivatives are considered up to the desired order, wherein the second derivatives describe the local curvature properties of the wavefront, and the higher derivatives coincide with the higher-order aberrations.

Given the calculation of light through the spectacles lens, up to the eye 12, according to the personalized prepared eye model, the local derivatives of the wavefronts are determined in the end effect at a suitable position in the ray path in order to compare them there with a reference wavefront which converges at a point on the retina of the eye 12. In particular, the two wavefronts (meaning the wavefront coming from the spectacles lens and the reference wavefront) are compared with one another at an evaluation surface.

What is thereby meant by "position" is thereby not simply a defined value of the z-coordinate (in the light direction), but rather such a coordinate value in combination with the specification of all surfaces through which refraction has taken place before reaching the evaluation surface. In a preferred embodiment, refraction occurs through all refracting surfaces, including the posterior lens surface. In this instance, a spherical wavefront whose center of curvature lies on the retina of the eye 12 preferably serves as a reference wavefront.

Particularly preferably, as of this last refraction propagation does not continue, so that the radius of curvature of this reference wavefront corresponds directly to the distance between posterior lens surface and retina. In an alternative possibility, propagation does continue after the last refraction, and in fact preferably up to the exit pupil AP of the eye 12. For example, this is situated at a distance $d_{AR} = d_{LR}^{(b)} = d_{LR} - d_{LR}^{(a)} > d_{LR}$ in front of the retina, and therefore even in front of the posterior lens surface, so that in this instance the propagation is a back-propagation (the terms $d_{LR}^{(a)}$, $d_{LR}^{(b)}$ are described further below in the enumeration of steps 1-6). In this instance as well, the reference wavefront is spherical with center of curvature on the retina, but has curvature radius $1/d_{AR}$.

In this regard, it is assumed that a spherical wavefront $w_0$ emanates from the object point and propagates up to the first spectacles lens surface 14. There it is refracted and subsequently propagates up to the second spectacles lens surface 16, where it is refracted again. The wavefront $w_{g1}$ exiting from the spectacles lens subsequently propagates along the principal ray in the direction of the eye 12 (propagated wavefront $w_{g2}$) until it strikes the cornea 18, where it is again refracted (wavefront $w_c$). After a further propagation within the anterior chamber depth up to the eye lens 20, the wavefront is also refracted again by the eye lens 20, whereby the resulting wavefront $w_e$ is created at the posterior surface of the eye lens 20 or at the exit pupil of the eye, for example. This is compared with the spherical reference wavefront $w_s$, and for all visual points the deviations are evaluated in the objective function (preferably with corresponding weightings for the individual visual points).

The ametropia is thus no longer described only by a thin sphero-cylindrical lens, as this was typical in many conventional methods; rather, the corneal topography, the eye lens, the distances in the eye, and the deformation of the wavefront (including the lower-order aberrations—thus sphere, cylinder, and axis length—as well as preferably also including the higher-order aberrations) in the eye are preferably directly considered.

An aberrometer measurement preferably delivers the personalized wavefront deformations of the real, ametropic eye for far and near (deviations, no absolute refractive powers), and the personalized mesopic and photopic pupil diameters. A personalized real anterior corneal surface that generally makes up nearly 75% of the total refractive power of the eye is preferably obtained from a measurement of the corneal topography (areal measurement of the anterior corneal surface). In a preferred embodiment, it is not necessary to measure the posterior corneal surface. Due to the small refractive index difference relative to the aqueous humor, and due to the small cornea thickness, it is preferably described in good approximation not by a separate refractive surface, but rather by an adaptation of the refractive index of the cornea.

In general, in this specification bold-face lowercase letters designate vectors, and bold-face capital letters designate matrices, for example the (2×2) vergence matrices or refractive index matrices $$S = \begin{pmatrix} S_{xx} & S_{xy} \\ S_{xy} & S_{yy} \end{pmatrix}, C = \begin{pmatrix} C_{xx} & C_{xy} \\ C_{xy} & C_{yy} \end{pmatrix}, L = \begin{pmatrix} L_{xx} & L_{xy} \\ L_{xy} & L_{yy} \end{pmatrix}, 1 = \begin{pmatrix} 1 & 0 \\ 0 & 1 \end{pmatrix},$$

and cursive letters such as d designate scalar values.

Furthermore, bold-face cursive capital letters should designate wavefronts or surfaces as a whole. For example, $\boldsymbol{S}$ is thus the vergence matrix of the identically named wavefront $\boldsymbol{S}$; aside from the 2nd-order aberrations that are encompassed in S, $\boldsymbol{S}$ also includes the entirety of all higher-order aberrations (HOAs) of the wavefront. Mathematically, $\boldsymbol{S}$ stands for the set of all parameters that are necessary in order to describe a wavefront (sufficiently precisely) with regard to a given coordinate system. $\boldsymbol{S}$ preferably stands for a set of Zernike coefficients having a pupil radius, or a set of coefficients of a Taylor series. $\boldsymbol{S}$ particularly preferably stands for the set from a vergence matrix S to describe the 2nd-order wavefront properties, and a set of Zernike coefficients (with a pupil radius) that serves to describe all remaining wavefront properties except for the 2nd order, or a set of coefficients according to a Taylor decomposition. Analogous statements apply to surfaces instead of wavefronts.

Among other things, the following data may in principle be measured directly:

the wavefront $S_M$, which is generated by the laser spot on the retina and the passage through the eye (from aberrometric measurement)

shape of the anterior corneal surface $\boldsymbol{C}$ (via corneal topography)

distance between cornea and anterior lens surface $d_{CL}$ (via pachymetry). This variable may also be determined indirectly via the measurement of the distance between the cornea and the iris; correction values may thereby be applied, if applicable. Such corrections may be the distance between the anterior lens surface and the iris, from known eye models (for example literature values).

curvature of the anterior lens surface in a direction $L_{1,xx}$ (via pachymetry). Without limitation of the generality, the x-plane may thereby be defined such that this section lies in the x-plane. The coordinate system is thus defined so that this plane lies obliquely; the derivative must be expanded by the functions of the corresponding angle. It is not required that it thereby be a principal section. For example, it may be the section in the horizontal plane.

Furthermore—depending on the embodiment—the following data may either be measured or learned from the literature:

thickness of the lens $d_L$ curvature of the posterior lens surface in the same direction as the anterior lens surface $L_{2,xx}$ (via pachymetry)

Therefore, there are the following possibilities for the posterior lens surface:

measurement of $L_{2,xx}$ ($L_{2,M}$) and assumption of a rotational symmetry $L_{2,xx}=L_{2,yy}=L_2=L_{2,M}$ and $L_{2,xy}=L_{2,yx}=0$ taking $L_{2,xx}$ from the literature ($L_{2,Lit}$), and assumption of a rotational symmetry $L_{2,xx}=L_{2,yy}=L_2=L_{2,M}$ and $L_{2,xy}=L_{2,yx}=0$ taking the complete (asymmetrical) shape $L_2$ from the literature ($L_{2,Lit}$)

measurement of $L_{2,xx}$ ($L_{2,M}$), and assumption of a cylinder or an otherwise specified asymmetry $a_{Lit}$ from the literature $L_{2,xx}=L_{2,M}$ and $L_{2,xy}=L_{2,yx}=f(L_{2,xx},a_{Lit})$ as well as $L_{2,yy}=g(L_{2,xx},a_{Lit})$ The following data may be learned from the literature:

refractive indices $n_{CL}$ of cornea and anterior chamber depth, as well as of the aqueous humor $n_{LR}$ and that of the lens $n_L$ In particular, the distance $d_{LR}$ between posterior lens surface and retina, as well as the components $L_{1,yy}$ and $L_{1,xy}=L_{1,yx}$ of the anterior lens surface, therefore remain as unknown parameters. To simplify the formalism, the former may also be written as a vergence matrix $D_{LR}=D_{LR}\cdot 1$ with $D_{LR}=n_{LR}/d_{LR}$. Furthermore, the variable z is generally used, which is defined as $\tau=d/n$ (wherein the corresponding index as is used for d and $\tau$ is always to be used for the refractive index as n, for example as $\tau_{LR}=d_{LR}/n_{LR}$, $\tau_{CL}=d_{CL}/n_{CL}$).

In a preferred embodiment in which the lens is described via an anterior surface and a posterior surface, the modeling of the passage of the wavefront through the eye model used according to the invention, thus after the passage through the surfaces of the spectacles lens, may be described as follows, wherein the transformations of the vergence matrices are explicitly indicated:

7. Refraction of the wavefront S with the vergence matrix S at the cornea C with the surface refractive power matrix C, relative to the wavefront $S'_C$ with vergence matrix $S'_C=S+C$ 8. Propagation by the anterior chamber depth $d_{CL}$ (distance between cornea and anterior lens surface) relative to the wavefront $S_{L1}$ with vergence matrix $S_{L1}=S'_C/(1-\tau_{CL}\cdot S')$ $$S_{L1} = \frac{S'_C}{(1-\tau_{CL}\cdot S'_C)}$$

9. Refraction at the anterior lens surface $L_1$ with the surface refractive power matrix $L_1$ relative to the wavefront $S'_{L1}$ with the vergence matrix $S'_{L1}=S_{L1}+L_1$ 10. Propagation by the lens thickness $d_L$ relative to the wavefront $S_{L2}$ with vergence matrix $S_{L2}=S'_{L1}/(1-\tau_L\cdot S'_{L1})$ 11. Refraction at the posterior lens surface $L_2$ with the surface refractive power matrix $L_2$ relative to the wavefront $S'_{L2}$ with the vergence matrix $S'_{L2}=S_{L2}+L_2$ 12. Propagation by the distance between lens and retina $d_{LR}$ relative to the wavefront $S_R$ with the vergence matrix $S_R=S'_{L2}/(1-\tau_{LR}\cdot S'_{L2})$ Each of the steps 2, 4, 6 in which propagation takes place over the distances $\tau_{CL}$, $\tau_{CL}$, or $\tau_{CL}$ may thereby be divided up into two partial propagations 2a,b), 4a,b), or 6a,b) according to the following scheme, which for step 6a,b) explicitly reads:

6a. Propagation by the distance $d_{LR}^{(a)}$ between lens and intermediate plane relative to the wavefront $S_{LR}$ with the vergence matrix $S_{LR}=S'_{L2}/(1-\tau_{LR}^{(a)}S'_{L2})$ 6b. Propagation by the distance $d_{LR}^{(b)}$ between intermediate plane and retina relative to the wavefront $S_R$ with the vergence matrix $S_R=S_{LR}/(1-\tau_{LR}^{(b)}S_{LR})$ $\tau_{LR}^{(a)}=d_{LR}^{(a)}/n_{LR}^{(a)}$ and $\tau_{LR}^{(b)}=d_{LR}^{(b)}/n_{LR}^{(b)}$ may thereby be positive or negative, wherein $n_{LR}^{(a)}=n_{LR}^{(b)}=n_{LR}$ and $\tau_{LR}^{(a)}+\tau_{LR}^{(b)}=\tau_{LR}$ should always be true. In each instance, step 6a and step 6b can be combined again via $S_R=S'_{L2}/(1-(\tau_{LR}^{(a)}+\tau_{LR}^{(b)})S'_{L2})=S'_{L2}/(1-\tau_{LR}S'_{L2})$. However, the division into step 6a and step 6b offers advantages, and the intermediate plane may preferably be placed in the plane of the exit pupil AP, which preferably is situated in front of the posterior lens surface. In this instance, $\tau_{LR}^{(a)}<0$ and $\tau_{LR}^{(b)}>0$.

The division of steps 2, 4 may also take place analogous to the division of step 6 into 6a,b).

For the selection of the evaluation surface of the wavefront, it is thus not only the absolute position in relation to the z-coordinate (in the light direction) but also the number of surfaces through which refraction has already taken place up to the evaluation surface. One and the same plane may thus be traversed repeatedly. For example, the plane of the AP (which normally is situated between the anterior lens surface and the posterior lens surface) is formally traversed by the light for the first time after a virtual step 4a, in which propagation takes place from the anterior lens surface by the length $\tau_L^{(a)}>0$. The same plane is reached for the second time after step 6a if, after refraction by the posterior lens surface, propagation takes place again back to the AP plane, meaning that $\tau_{LR}^{(a)}=-\tau_L+\tau_L^{(a)}=-\tau_L^{(b)}<0$, which is equivalent to $\tau_{LR}^{(a)}=\tau_{LR}-\tau_{LR}^{(b)}<0$. Given the wavefronts $S_{AP}$, which relate in the text to the AP, what should preferably always be meant (if not explicitly noted otherwise) is the wavefront $S_{AP}=S_{LR}$, which is the result of step 6a.

These steps 1 through 6 are referred to repeatedly in the further course of the specification. They describe a preferred correlation between the vergence matrix S of a wavefront S at the cornea and the vergence matrices of all intermediate wavefronts arising therefrom at the refractive intermediate surfaces of the eye, in particular the vergence matrix $S'_{L2}$ of a wavefront $S'_{L2}$ after the eye lens (or even of a wavefront $S_R$ at the retina). These correlations may be used both to calculate parameters (for example $d_{LR}$ or $L_1$) that are not known a priori, and thus to populate the model with values in either a personalized or generic manner, and in order to simulate the propagation of the wavefront in the eye with then populated models to optimize spectacles lenses.

Before the procedure according to the invention of the consideration of higher-order aberrations (meaning higher than second order, in particular in Taylor or Zernike decomposition of the aberrations) is discussed, for the sake of simplicity in the following an example of a principle of the formalism should be described using a description of the surfaces and wavefronts up to the second order, for which a representation by vergence matrices is sufficient. As is subsequently presented, this formalism may be used analogous to that for the implementation of the invention under consideration of higher orders of aberrations.

In a preferred embodiment, in a second-order description the eye model has twelve parameters as degrees of freedom of the model that need to be populated. These preferably include the three degrees of freedom of the surface refractive power matrix C of the cornea C; the respective three degrees of freedom of the surface refractive power matrices $L_1$ and $L_2$ for the anterior lens surface or posterior lens surface; and respectively one for the length parameters of anterior chamber depth $d_{CL}$, lens thickness $d_L$, and the vitreous body length $d_{LR}$.

Populations of these parameters may in principle take place in a plurality of ways:

iv) directly, thus personalized measurement of a parameter v) a priori given value of a parameter, for example as a literature value or from an estimate, for example due to the presence of a measured value for another variable that correlates with the parameter to be determined in a known manner using a preceding population analysis vi) calculation from consistency conditions, for example compatibility with a known refraction The total number $df_2$ of second-order degrees of freedom of the eye model (df stands for "degree of freedom", the index "2" stands for 2nd-order) is thus composed of $$df_2 = df_2(i) + df_2(ii) + df_2(iii)$$

For example, if direct measured values are present for all twelve model parameters, then $df_2(i)=12$, $df_2(ii)=0$, and $df_2(iii)=0$, which for the sake of simplicity is expressed in the following by the notation $df_2=12+0+0$. In such an instance, the object refraction of the appertaining eye is also established, so that an objective refraction determination would no longer need to be additionally implemented.

For the implementation of the present invention, it is not necessary to directly measure all parameters. Under the circumstances, it is thus simpler to measure, or objectively and/or subjectively determine, the refraction of the appertaining eye than to measure all parameters of the model eye in a personalized manner. At least one refraction, thus measurement data regarding the wavefront $S_M$ of the eye up to the 2nd order that correspond to the data of the vergence matrix $S_M$, is thus preferably present. Given a population of the eye model purely on the basis of objectively measured data, these values may be taken from autorefractometric measurements, for example, or according to (ii) may be populated by data provided otherwise. The three conditions of the agreement with the three independent parameters of the vergence matrix $S_M$ therefore allow three parameters of the eye model to be derived, which in the notation introduced above corresponds to $df_2(iii)=3$.

In instances in which not all model parameters are accessible to direct measurements, or these measurements would be very costly, it is thus possible to reasonably populate the missing parameters. For example, if direct measured values are present for at most nine model parameters ($df_2(i) \leq 9$), then the cited conditions of the refraction may be used in order to calculate three of the model parameters ($df_2(iii)=3$). In the event that $df_2(i)=9$ applies exactly, all twelve model parameters are then determined unambiguously via the measurements and the calculation, and ($df_2(ii)=0$) applies. By contrast, if $df_2(i)<9$, then $df_2(ii)=9-df_2(i)>0$, meaning that the model is underdetermined in the sense that $df_2$ (ii) parameters need to be established a priori.

With the provision of a personalized refraction, thus measurement data regarding the wavefront $S_M$ of the eye, in particular up to the second order, the necessary data of the vergence matrix $S_M$ are present. According to a conventional method described in WO 2013/104548 A1, in particular the parameters $\{C, d_{CL}, S_M\}$ are measured. By contrast, among other things the two length parameters $d_L$ and $d_{LR}$ (or $D_{LR}$) are conventionally established a priori (for example via literature values or estimation). In WO 2013/104548 A1, in particular a differentiation is made between the two instances in which either $L_2$ is established a priori and $L_L$ is calculated therefrom, or vice versa. The cited disclosure document discloses Equation (4) or Equation (5) as a calculation rule in this regard. For both instances, $df_2=4+5+3$ applies.

In the terminology of the aforementioned steps 1 through 6, the adaptation of $L_1$ to the measurements in particular occurs in that, on the one hand, the measured vergence matrix $S_M$ is calculated through the likewise measured matrix C by means of the steps 1, 2, and propagated up to the object-side side of the anterior lens surface. On the other hand, a spherical wave is calculated from back to front from an imaginary point light source on the retina by means of the steps 6, 5, 4, run through in reverse, in that this spherical wave is refracted at the previously established surface refractive power matrix $L_2$ of the posterior lens surface, and the wavefront that is then obtained propagates from the posterior lens surface up to the image-side side of the anterior lens surface. The difference of the vergence matrices $S_{L1}$ and $S'_{L1}$ that are determined in this manner, which difference must be present on the object side or image side of the anterior lens surface, must have been produced by the matrix $L_1$, because in the aberrometric measurement the measured wavefront arises from a wavefront that emanates from a point on the retina and therefore, due to the reversibility of the ray paths, is identical to that incident wavefront ($S=S_M$) that converges on this point of the retina. This leads to Equation (4) in the cited disclosure document:

$$L_1(D_{LR}) = \frac{D_{LR} \cdot 1 - L_2}{1 + \tau_L \cdot (D_{LR} \cdot 1 - L_2)} - \frac{S_M + C}{1 - \tau_{CL}(S_M + C)} \quad (1a)$$

The other instance in the cited disclosure document relates to the adaptation of the matrix $L_2$ to the measurements after the matrix $L_1$ has been established. A difference now exists merely in that: the measured wavefront $S_M$ is subjected to the steps 1, 2, 3, 4, and the assumed wavefront from the point light source is only subjected to step 6; and in that the missing step that is to take place for adaptation of the posterior lens surface $L_2$ is now step 5, corresponding to Equation (5) of the cited disclosure document:

$$L_2 = D_{LR} - \left(\frac{S_M + C}{1 - \tau_{CL}(S_M + C)} + L_1\right)\left(1 - \tau_L\left(\frac{S_M + C}{1 - \tau_{CL}(S_M + C)} + L_1\right)\right)^{-1} \quad (1b)$$

In a preferred implementation of the invention, at least one of the length parameters $d_L$ and $d_{LR}$ (or $D_{LR}$) is calculated from other measured data and a priori assumptions regarding other degrees of freedom, and in particular is not assumed a priori.

The data of the vergence matrix $S_M$, and particularly preferably also the data regarding C from personalized measurements, are preferably available. In a further preferred embodiment, a spherical posterior surface, meaning a posterior surface without astigmatic components, is assumed given an assumption of data regarding the posterior lens surface.

In a preferred embodiment of the invention, measurement data up to the second order that corresponding to the data of the surface refractive power matrix C are thus present with regard to the cornea C. Although these values may be learned from topographical measurements, the latter are not necessary. Rather, topometric measurements are sufficient. This situation corresponds to the instance $df_2=3+6+3$, wherein in particular the anterior chamber depth $d_{CL}$ is one of the six parameters that are to be established a priori.

Insofar as no further personalized measurements are performed, a situation with $df_2=3+6+3$ is present. In order to be able to unambiguously determine $d_{LR}$, six parameters from $\{L_1, L_2, d_L, d_{CL}\}$ must thus be populated via assumptions or literature values. The remaining two result from the calculation in addition to $d_{LR}$. In a preferred embodiment, the parameters of the posterior lens surface, the mean curvature of the anterior lens surface, and the two length parameters $d_L$ and $d_{CL}$ are populated a priori (as predetermined standard values).

In a preferred implementation, the anterior chamber depth $d_{CL}$ is thus additionally the distance between the cornea and the anterior lens surface, known for example from pachymetric or OCT measurements. The measured parameters therefore include $\{C, d_{CL}, S_M\}$. This situation corresponds to the instance of $df_2=4+5+3$. Afterward the problem is still mathematically underdetermined; five parameters must thus be established a priori from $\{L_1, L_2, d_L\}$ via assumptions or literature values. In a preferred embodiment, the parameters are hereby the posterior lens surface, the mean curvature of the anterior lens surface, and the lens thickness. The precise way of calculating for this instance is presented in more detail further below.

Solely for the precision of the personalized adaptation, it is advantageous to be able to populate as many parameters as possible with personalized measurements. In a preferred embodiment, for this purpose the lens curvature is additionally provided in a normal section on the basis of a personalized measurement. A situation according to $df_2=5+4+3$ then thereby results, and it is sufficient to establish four parameters from $\{L_{1yy}, \alpha_{L1}, L_2, d_L\}$ a priori. Here as well, in a preferred embodiment these are again the parameters of posterior lens surface and the lens thickness. The precise calculation is again described in more detail further below.

In particular as an alternative to the normal step of the anterior lens surface, and particularly preferably in addition to the anterior chamber depth, the lens thickness may also be provided from a personalized measurement. The necessity to populate these parameters with model data or estimated parameters thereby disappears $((df_2=5+4+3))$. Otherwise, the statements as already made above apply. This embodiment is particularly advantageous if a pachymeter is used whose measurement depth allows the detection of the posterior lens surface, but not a sufficiently certain determination of the lens curvatures.

In addition to the anterior chamber depth and a normal section of the anterior lens surface, in a preferred embodiment one additional parameter (for example measurement in two normal sections) or two additional parameters (measurement of both principal sections and the axis position) of the anterior lens surface are recorded via a personalized measurement. This additional information may in particular be utilized in two ways:

Abandonment of a priori assumptions: one or two of the assumptions that were otherwise made a priori may be abandoned and be determined via calculation. In this instance, the situations $df_2=6+3+3$ or $df_2=7+2+3$ result. In the first instance, the mean curvature of the posterior surface (given assumption of an astigmatism-free posterior surface) may be determined, and in the second instance the surface astigmatism (including axis position) may be determined for a given mean curvature. Alternatively, in both instances the lens thickness may be determined from the measurements.

However, such a procedure generally requires a certain caution, since noisy measurement data may easily lead to a "runaway" of the enabled parameters. The model may thereby as a whole become markedly worse instead of better. One possibility to prevent this is to predetermine anatomically reasonable limit values for these parameters, and to limit the variation of the parameters to this range. Of course, these limits may also be predetermined depending on the measured values.

Reduction of the measurement uncertainty: if, by contrast, the same a priori assumptions continue to be made (preferably thus $\{L_2, d_L\}$), the situations $df_2=6+4+3$ or $df_2=7+4+3$ are present; the system is thus mathematically overdetermined.

Instead of a simple analytical determination of $D_{LR}$ according to the subsequent embodiments, $D_{LR}$ (and possibly the still missing parameters from $L_1$) is determined ("fit") so that the distance between the $L_1$ resulting from the equations and the measured $L_1$ (or the measured $L_1$, supplemented by the missing parameters) is minimal. A reduction of the measurement uncertainty may—obviously—be achieved via this procedure.

In a further preferred implementation, the anterior chamber depth, two or three parameters of the anterior lens surface, and the lens thickness are measured in a personalized manner. The calculation of the remaining variables thereby takes place analogously, wherein the a priori assumption of the lens thickness may be replaced by the corresponding measurement.

In a further preferred implementation, personalized measurements of the anterior chamber depth, at least one parameter of the anterior lens surface, the lens thickness, and at least one parameter of the posterior lens surface are provided. This is hereby an expansion of the aforementioned instances. The respective additionally measured parameters may take place analogous to the step-by-step expansions of the above segments. These instances are particularly advantageous if the aforementioned pachymetry units that measure in one plane, two planes, or over the entire surface are accordingly extended in terms of measurement depth, and are so precise that the curvature data can be sufficiently precisely determined.

In the following it is shown, using a few examples, how the calculation of individual parameters may take place from the remaining measured parameters or parameters established a priori, and using the personalized refraction data.

For example, in preferred embodiments, a measurement of the curvature of a lens surface is available in a normal section. Since the posterior surface cannot be measured in practice without the anterior surface also being measured, and the measurement of the anterior surface preferably occurs, the equations for the instances of a curvature of the anterior lens surface that is known in a normal section are specified in the following. If, instead of a normal section of the anterior lens surface, a normal section of the posterior lens surface is present (for example corresponding measurements, model assumptions), one must analogously proceed with Equation (1b). Without limiting the generality, the coordinate system is placed so that the normal section travels in the x-direction. In a next step, the matrix equation (1a) is then evaluated in the given normal section and solved for $D_{LR}$, and this solution is subsequently used again in Equation (1a) for the complete specification of $L_1$.

If the xx-component of $L_1(D_{LR})$ from Equation (1) is set equal to the measured value $L_{1,xx}$, for this matrix element a quadratic equation in $D_{LR}$ is obtained whose positive solution corresponds to the distance between posterior lens surface and retina:

$$D_{LR} = \frac{-b + \sqrt{b^2 - 4c}}{2a} \quad (2)$$

It thereby applies that:

$a = \tau_L(1 + \tau_L A)$ $b = 1 - \tau_L(tr(L_2) - AB)$ $c = A - L_{2,xx} + \tau_L \det L_2(1 + \tau_L A) - \tau_L A \, tr(L_2) = A - L_{2,xx} + a \det L_2 - \tau_L A \, tr(L_2)$ \quad (2a)

with $A = -S_{M,L1,xx} - L_{1,xx}$ $B = 2 - \tau tr(L_2)$ $\det(L_2) = L_{2,xx} L_{2,yy} - L_{2,xy}^2$ $tr(L_2) = L_{2,xx} + L_{2,yy}$ \quad (2b)

and $$S_{M,L1,xx} = \frac{\tau_{CL} S'^2_{M,C,xy} + S'_{M,C,xx} \cdot (1 - \tau_{CL} S'_{M,C,yy})}{-\tau_{CL}^2 S'^2_{M,C,xy} + (1 - \tau_{CL} S'_{M,C,xx}) \cdot (1 - \tau_{CL} S''_{M,C,yy})} \quad (2c)$$

$S'_{M,C,xx} = S_{M,xx} + C_{xx}$ (xy und yy analog)

In the event of a symmetrical posterior lens surface ($L_2 = L_{2,xx} \cdot 1$), this simplifies to $$D_{LR} = L_{2,xx} + \frac{L_{1,xx} + S_{M,L1,xx}}{1 - \tau_L \cdot (L_1 + S_{M,L1,xx})} \quad (3)$$

with $S_{M,L1,xx}$ from Equation (2c).

In both instances, it is therefore possible to calculate the anterior lens surface $L_1$ in that the respectively obtained $D_{LR}$ in Equation (1a) is used:

$$L_1 = \frac{D_{LR} - L_2}{1 + \tau_L \cdot (D_{LR} - L_2)} - \frac{S_M + C}{1 - \tau_{CL}(S_M + C)} \quad (4)$$

The result is naturally symmetrical ($L_{1,xy} = L_{1,yx}$), and for the component $L_{1,xx}$ reproduces the value used in (2b) or (3).

In some preferred embodiments, a personalized measurement or a specification of a mean curvature of a lens surface is provided. For example, this situation is present when the mean curvature of the anterior lens surface may be measured, or no measurements at the lens surfaces may be performed and the mean curvature of a lens surface is assumed (for example taken from the literature). As was just now described, here the method for the anterior lens surface is described and can be analogously transferred to the posterior lens surface.

In this instance of a given mean sphere $L_{1,ms}$ of the anterior lens surface, the free parameters are the cylinder $L_{1,cyl}$ and the axis length $\alpha_{L1}$. With $L_{1,diff} = L_{1,cyl}/2$, $L_1$ becomes $$L_1 = \begin{pmatrix} L_{1,ms} - L_{1,diff} \cdot \cos 2\alpha_{L1} & -L_{1,diff} \cdot \sin 2\alpha_{L1} \\ -L_{1,diff} \cdot \sin 2\alpha_{L1} & L_{1,ms} + L_{1,diff} \cdot \cos 2\alpha_{L1} \end{pmatrix} \quad (5)$$

One again proceeds from Equation (1a). If the expressions for $L_1$ from Equations (5) and (1a) are now equated, an equation system is obtained that is made up of three equations (the two non-diagonal elements are identical) and the three unknowns $L_{1,diff}$, $\alpha_{L1}$ and $D_{LR}$. This has the physically relevant solution $$D_{LR} = \frac{-\bar{b} + \sqrt{\bar{b}^2 - 4\bar{a}\bar{c}}}{2\bar{a}} \quad (6)$$

$L_{1diff} = \pm \sqrt{\sigma^2 + \gamma^2}$ $\alpha_{L1} = \frac{1}{2} \arctan(\pm \gamma, \pm \sigma) + \frac{\pi}{2}$ with $\bar{a} = \tau_L(1 + \tau_L \bar{A})$ \quad (6a)

$\bar{b} = 1 - \tau_L(tr(L_2) - \bar{A}B)$ $\bar{c} = \frac{1}{4}(\bar{A}B^2 - B tr(L_2) - \bar{a} Ast(L_2)^2)$ and $\bar{A} = \bar{S}_{M,L1} - \bar{L}_{1,mess}$ $Ast(L_2) = \sqrt{tr(L_2)^2 - 4 \det L_2}$ $\gamma = \frac{2(-1 + \sqrt{\bar{b}^2 - 4\bar{a}\bar{c}})(L_{2,xx} - L_{2,xy}) + \tau_L^2 Ast(L_2)^2 (S_{M,L1,xx} - S_{M,L1,yy})}{2\tau_L^2 Ast(L_2)^2}$ $\sigma = \frac{2(-1 + \sqrt{\bar{b}^2 - 4\bar{a}\bar{c}})L_{2,xy} + \tau_L^2 Ast(L_2)^2 S_{M,L1,xy}}{2\tau_L^2 Ast(L_2)^2}$ This can also be simplified for the instance of a rotationally symmetrical posterior lens surface:

$$D_{LR} = L_2 + \frac{\bar{L}_{1,mess} + \bar{S}_{M,L1}}{1 - \tau_L \cdot (\bar{L}_{1,mess} + \bar{S}_{M,L1})} \quad (7)$$

$L_1 = (\bar{L}_{1,mess} + \bar{S}_{M,L1}) \cdot 1 - \frac{S_M + C}{1 - \tau_{CL}(S_M + C)}$ wherein $\bar{L}_{1,meas} = \frac{D_{LR} - L_2}{1 + \tau_L \cdot (D_{LR} - L_2)} - \bar{S}_{M,L1}$ with $\bar{S}_{M,L1} = \frac{S_{M,L1,xx} + S_{M,L1,yy}}{2}$ The individual elements of the eye model can therefore be entirely calculated.

Aside from a principal section with given angle position, or the mean curvature, the given (i.e. measured or assumed) variables may also be other parameters such as the thickest principal section, the thinnest principal section, the cylinder, and the axis position. In these instances, the procedure is analogous to the illustrated instances.

Since the HOAs of the eye have also be now been taken into account in the optimization of spectacles lenses, it is advantageous to also consider the HOAs of the cornea or of the lens in the population of the eye model. Given the selection of HOAs for the lens, it generally applies that HOAs that may also represent the refractive index curve within the lens may be associated with the anterior lens surface or posterior lens surface.

The previously depicted formalism is preferably expanded, in particular with regard to the cited steps 1 through 6, to the co-treatment of the HOAs, in that the calculation methods from the publications by G. Esser et al.: "Derivation of the refraction equations for higher order aberrations of local wavefronts at oblique incidence", JOSA A, Vol. 27, No. 2 (2010), and by G. Esser et al.: "Derivation of the propagation equations for higher order aberrations of local wavefronts", JOSA A, Vol. 28, No. 11 (2011), are applied aside from the formulas for the vergence matrices that are explicitly specified in steps 1 through 6.

In general, the procedure with regard to the enumeration of degrees of freedom is executed in a manner very similar to as above. If, aside from data regarding 2nd-order errors, data about their HOAs are present (either from measurements or from reasonable assumptions) with regard to refractive surface C of the cornea and regarding the outgoing wavefront $S_M$, the wavefront $S_{L1}$ may also be determined computationally with accordingly many HOAs. This applies independently of the form in which the HOAs present themselves. However, the Taylor series is particularly preferred, because in this form the statement exactly applies: if HOA coefficients up to the n-th order are present with regard to two surfaces C and $S_M$, the corresponding HOA coefficients for $S_{L1}$ can then also be computationally determined therefrom up to the n-th order. Furthermore, the Zernike basis is preferred, because here as well a similar statement applies. However, this is exact only when all Zernike coefficients with an order >n vanish.

An order n is preferably established (in advance), up to which all participating surfaces and wavefronts should be treated. Independently of the presentation of the HOAs, aside from the three components for the 2nd-order errors, the wavefronts or surfaces then additionally possess N components for the HOAs, wherein N depends on n and, inter alia, on the presentation form of the HOAs (in the Taylor decomposition and Zernike decomposition, $N=(n+1)(n+2)/2-6$ applies).

The adaptation condition using a measured wavefront, for example $S_{M,L1}$, then also accordingly no longer possesses only the three components described above, but rather a maximum of N+3 components in total. These are then accordingly accompanied by 3·(N+3)+3=3N+12 parameters (namely the three length parameters $d_{CL}$, $d_L$ and $d_{LR}$ (or $D_{LR}$), as well as respectively N+3 components of the cornea C and the lens surfaces $L_1$ and $L_2$). This means that $$df_n = df_n(i) + df_n(ii) + df_n(iii)$$
$$= 3N + 12$$

applies, with $df_n(iii)=N+3$. If the anterior chamber depth $d_{CL}$ and the cornea C are preferably measured again, $df_n(i)=N+4$ applies, and consequently $df_n(ii)=N+5$, corresponding to the situation of $df_n=(N+4)+(N+5)+(N+3)$.

The further procedure may be implemented in a manner very analogous to as described above.

In principle, the HOAs of the mapping of the eye onto the retina may be detected in transmission via suitable measurement devices with an aberrometry unit. On the other hand, the HOAs of the cornea surface may be measured in reflection by a topography unit. Both data of the exiting wavefront $S_M$ and a description of the refracting surface C of the cornea, including the HOAs up to a defined order n, are therefore available.

In the event of a measurement of the $S_M$ for HOAs as well, this supplies $df_n(iii)=N+3$ conditions for parameter calculation. If it is again preferred to also measure the $d_{CL}$ in addition to the cornea C, $df_n(i)=N+4$ applies, and consequently $df_n(ii)=N+5$, corresponding to the situation $df_n=(N+4)+(N+5)+(N+3)$.

In such an instance, in the population of the model, the HOAs of the lens may be selected so that the measured wavefront is created given the propagation of a wavefront emanating from a point of the retina according to steps 1 through 6, in reverse order. If the parameters of the eye model are then populated, the propagation of this wavefront, emanating from a point of the retina up to the evaluation surface (according to at least one of the steps 1 through 6, in reverse order) may lead to the reference wavefront, which then is used for a comparison with the wavefront emanating from an object.

In principle, in the adaptation of $L_1$ the method may proceed analogous to the method described above with reference to WO 2013/104548 A1, wherein the two length parameters $d_L$ and $d_{LR}$ (or $D_{LR}$) are established a priori. The single difference is now that the anterior lens surface $L_1$, including its N HOA parameters up to the n-th order, may be adapted to the measurements, corresponding to $df_n(iii)=N+3$. The posterior lens surface $L_2$, which is unknown due to a lack of measured values, is preferably established in advance (for example via literature values regarding the average eye of the general population), including the N HOA parameters up to the n-th order, corresponding to $df_n(ii)=N+5$. This occurs in particular in that, on the one hand, the measured wavefront $S_M$ is calculated through the likewise measured cornea C by means of steps 1, 2, and propagates up to the object-side side of the anterior lens surface $L_1$. On the other hand, a spherical wave is calculated from back to front, by means of the steps 6, 5, 4 run through backward, from an imaginary point light source on the retina, in that this spherical wave refracts at the pre-established posterior lens surface $L_2$, and the wavefront that is then obtained propagates from the posterior lens surface up to the image-side side of the anterior lens surface $L_1$. The two wavefronts $S_{L1}$ and $S'_{L1}$ that are so determined, which are situated on the object side or, respectively, image side of the anterior lens surface, generally possess both lower-order aberrations and HOAs; however, their values differ between the two wavefronts. Since the two wavefronts occur in one and the same measurement ray path, and therefore must coincide beyond the still absent step 3, the refractive anterior lens surface $L_1$ may be concluded unambiguously from this difference up to the n-th order, and in fact via the calculation methods known from G. Esser et al.: "Derivation of the refraction equations for higher order aberrations of local wavefronts at oblique incidence", JOSA A, Vol. 27, No. 2 (2010), and from G. Esser et al.: "Derivation of the propagation equations for higher order aberrations of local wavefronts", JOSA A, Vol. 28, No. 11 (2011), for example.

On the other hand, in the adaptation of $L_2$ it is also possible to proceed analogous to the method described above with regard to WO 2013/104548 A1, wherein again the two length parameters $d_L$ and $d_{LR}$ (or $D_{LR}$) are established a priori. The posterior lens surface $L_2$, including its HOAs up to the n-th order, is now adapted to the measurements after the anterior lens surface $L_1$ has been established. A difference with regard to the adaptation of $L_1$ in particular exists in that the measured wavefront $S_M$ is subjected to steps 1, 2, 3, 4, and the assumed wavefront from the point light source is only subjected to step 6, and in that the missing step that is to take place to adapt the posterior lens surface $L_2$ is now step 5.

For calculation, the formalism described in G. Esser et al.: "Derivation of the refraction equations for higher order aberrations of local wavefronts at oblique incidence", JOSA A, Vol. 27, No. 2 (2010), and in G. Esser et al.: "Derivation of the propagation equations for higher order aberrations of local wavefronts", JOSA A, Vol. 28, No. 11 (2011), for example, is thereby used for the refraction steps or propagation steps. In particular, it is reasonable to work from the lowest-order aberrations to the highest-order aberrations of interest (typically sixth).

To use the aforesaid formalism, it is advantageous to describe the wavefronts or surfaces via the local derivation of the rise in the direction of the planes orthogonal to the direction of the propagation. Every surface or wavefront that is not present in this form is preferably initially brought into this form. For example, this may occur via transformation from a Zernike representation to the representation via local derivatives, or via a preceding fit of a rise representation. A suitable technical form of presentation of surfaces via Taylor coefficients is described in WO 2013/104548 A1, for example.

Naturally, the deviations (including the second-order aberrations may also be distributed among the anterior lens surface and posterior lens surface, analogous to the above procedure.

In a preferred embodiment, it is proposed that at least one of the length parameters $d_L$ and $d_{LR}$ is neither predetermined a priori nor measured in a personalized manner, but rather is calculated using the personalized refraction data and the other (pre-)established data. For this purpose, at least one measured value or an assumption is provided for one of the degrees of freedom of the lens surfaces $L_1$ or $L_2$. For example, if this is a measured value for the curvature of $L_1$ in a normal section, then in particular $d_{LR}$ (or $D_{LR}$) may be determined therefrom via calculation.

If the specification in the vergence matrices refers to the local curvature (thus corresponds to the specification of the HOAs as coefficients of a Taylor decomposition), for this purpose $D_{LR}$ and the missing parameters of the lens are first determined as has already been described above. Following this, the HOAs of the lens may then be constructed step by step, starting from the second to n-th order, with the formalism from G. Esser et al.: "Derivation of the refraction equations for higher order aberrations of local wavefronts at oblique incidence", JOSA A, Vol. 27, No. 2 (2010), and by G. Esser et al.: "Derivation of the propagation equations for higher order aberrations of local wavefronts", JOSA A, Vol. 28, No. 11 (2011).

By contrast to this, if the mean curvature over a defined pupil is used, which is the case given the representation according to Zernike, the degree of freedom $D_{LR}$ is likewise established. In this formalism, an iterative procedure would be necessary due to the dependencies. However, this can be avoided via a conversion between the two notations before the beginning of the calculation.

In principle, the HOAs of the mapping of the eye onto the retina may be detected in transformation via suitable measurement devices having an aberrometry unit. However, such aberrometry units for the detection of HOAs are quite expensive and are not available to every optometrist. However, it is often possible to measure the HOAs of the corneal surface in reflection at less cost via a topography unit. Therefore, although no data of the exiting wavefront $S_M$ are available, at least a description of the refracting surface C of the cornea is available, including the HOAs up to a defined order n.

The invention offers the possibility to use the personalized eye model if, although personalized measurements regarding the HOAs of the cornea are present, no personalized measurements of the HOAs of the eye are present. In a preferred implementation, aside from the cornea C, the anterior chamber depth $d_{CL}$ is thereby also measured, meaning that $df_n(i)=N+4$ applies. Given use of an autorefractometer (meaning no measurement of the HOAs) instead of an aberrometer (also in combination with a subjective refraction), or the sole use of a subjective refraction without use of an aberrometer or autorefractometer, although the vergence matrix $S_M$ of the LOAs is known, no personalized information about the HOAs of the (measurement ray path) wavefront $S_M$ of the entire eye is present. This means that, exactly as in the instance without HOAs, instead of $df_n=N+3$ calculation conditions only $df_n(iii)=3$ calculation conditions are present. If it is desired to completely populate the model up to the n-th order, instead of $df_n(ii)=N+5$ parameters $df_n(ii)=2N+5$ parameters are preferably accordingly established a priori. The instance is thereby preferably considered again that both $d_L$ and $d_{LR}$ belong among the parameters established a priori. The model can therefore be populated in different ways with the additional parameters and be used for the calculation and optimization of a spectacles lens.

In particular, this instance can be treated just as described above given the presence of measured HOAs of the eye, if assumptions are made about the HOAs of the eye. One example of this is values determined or model-based using a test subject collective. A remaining spherical aberration is thereby preferably assumed, since it is known—in particular from T. O. Salmon and C. van de Pol: *Normal-eye Zernike coefficients and root-mean-square wavefront errors*, J Cataract Refract Surg, Vol. 32, Pages 2064-2074 (2006), and from J. Porter et al.: *Monochromatic aberrations of the human eye in a large population*, JOSA A. Vol. 18, No. 8 (2001)—that this differs markedly from zero on average across the population. The calculation of the HOAs of the lens then takes place very analogously to the procedure described above, with the single difference that the HOA values for $S_M$ are not learned from a personalized measurement but rather are based on the aforementioned assumptions.

Alternatively, if suitable assumptions are made about the HOAs of the lens, meaning that the HOAs of both lens surfaces $L_1$ and $L_2$ are established a priori, the HOAs of the wavefront $S_M$ up to the n-th order may take place with, for example, the algorithms from G. Esser et al.: "Derivation of the refraction equations for higher order aberrations of local wavefronts at oblique incidence", JOSA A, Vol. 27, No. 2 (2010), and from G. Esser et al.: "Derivation of the propagation equations for higher order aberrations of local wavefronts", JOSA A, Vol. 28, No. 11 (2011), in that steps 6, 5, 4, 3, 2, 1 are traversed in reverse from the retina to the cornea. In particular, $d_L$ and $d_{LR}$ established a priori also thereby enter into the calculation of $S_M$.

For the LOAs of the lens surfaces, no a priori establishments are made that exceed the above statements, since the LOAs of the wavefront $S_M$ are present, for example as a measured vergence matrix $S_M$, from the subjective refraction, the autorefractor measurement, or a combination thereof.

A preferred embodiment instance is hereby that the HOAs of the lens surfaces are set equal to zero in the basis that is used. This assumption is particularly preferably made in relation to the Taylor basis. This assumption is furthermore preferred in relation to the Zernike basis. Although the HOAs of $S_M$ are not a basis for a direct mapping of the HOAs of C, because the participating propagations in each instance also introduce HOAs, the advantage of vanishing HOAs of the lens surfaces exists in the reduction of the computation cost due to numerous vanishing terms.

Alternatively, model-based values for the HOAs of the lens surfaces may also be selected. This applies in particular to spherical aberrations, in particular since it is known—from T. O. Salmon and C. van de Pol: *Normal-eye Zernike coefficients and root-mean-square wavefront errors*, J Cataract Refract Surg, Vol. 32, Pages 2064-2074 (2006), and from J. Porter et al.: *Monochromatic aberrations of the human eye in a large population*, JOSA A, Vol. 18, No. 8 (2001)—that the spherical aberration of the lens is on average markedly different than zero across the population. These may thereby be selected independently of the measured data, or depending on measured data (for example refraction values, spherical aberration of the cornea).

Even if neither a topograph nor an aberrometer is used, thus no personalized measurement data of the HOAs are present, model-based assumptions about the HOAs of the cornea, the lens, or the eye may nevertheless be made and be used in the population of the eye model. The assumed values may thereby also be selected using corresponding models, depending on measured data (for example refraction values, results of the topometry measurement or autorefractometer measurement). Examples of the precise calculation have already been described further above, wherein the corresponding assumptions apply instead of the measured values for the HOAs. This also applies again in particular to spherical aberrations, since these are on average markedly different from zero across the population. This may thereby be chosen independently of the measured data, or depending on measured data (for example refraction values, results of the topometry measurement or autorefractometer measurement) and be associated with the cornea, one of the two lens surfaces, or combinations.

The present invention offers the possibility of concluding $S_M$ via measurements of or assumptions about $L_1$ and $L_2$. Reasonable values for the HOAs of $S_M$ are thus obtained without aberrometric measurements. For this purpose, precise knowledge about the length parameters $d_L$ and $d_{LR}$ (or $D_{LR}$) also do not need to be present, so that the formalism can be used even without the calculation of $d_{LR}$ that is described in Section 3. In contrast to the second-order errors of the wavefront $S_M$, the HOAs of $S_M$ namely depend only so weakly on the length parameters $d_L$ and $d_{LR}$ (or $D_{LR}$) that the selection of the values for $d_L$ and $d_{LR}$ that are to be established a priori—within the scope of the physiologically reasonable range—for adaptation of the HOAs of $S_M$ has only a small influence, and consequently standard parameters may also be used.

One application of this method is that spectacles lens optimizations under consideration of the HOAs of the eye, such as the DNEye optimization, may be performed even without personalized aberrometric measurements (for example on the basis of topography measurements).

The evaluation of the aberrations during the calculation method or optimization method may be performed at different locations in the ray path, meaning that the evaluation surface may be provided at different positions. Instead of taking place at the retina or at the posterior lens surface, an evaluation of the imaging wavefront may also be already take place at a surface situated further forward in the model eye. For this purpose, within the model eye a reference wavefront R is defined that is then used in the lens optimization, for example. This reference wavefront thereby has the property that it leads to a point image given further propagation through the eye, up to the retina. Accordingly, the reference wavefront may be determined via back-propagation of a wavefront, which wavefront converges at a point on the retina, from the retina up to the position of the reference wavefront. For example, since the measured wavefront $S_M$ is precisely the wavefront that emanates from a point light source on the retina, this may also instead be propagated inside the eye, up to the position of the reference wavefront.

Considered mathematically, both procedures are equivalent and lead to the same formulas for the reference wavefront. In the following, to derive the corresponding reference wavefronts the respective way is chosen that manages with fewer propagation steps and enables a simpler representation. In the following, only the treatment of the components of the defocus and astigmatism is described by way of example. However, an extension to HOAs and the use of the subjective refraction is likewise possible and advantageous.

Given the consideration of HOAs, analogous to the calculation of the HOAs according to the embodiments below, this may take place via refraction (G. Esser et al.: "Derivation of the refraction equations for higher order aberrations of local wavefronts at oblique incidence", JOSA A, Vol. 27, No. 2 (2010)) and propagation (G. Esser et al.: "Derivation of the propagation equations for higher order aberrations of local wavefronts", JOSA A, Vol. 28, No. 11 (2011)).

Since the wavefront propagation is a non-linear process, a spectacles lens optimization that evaluates an imaging wavefront via comparison with a reference wavefront generally leads to different results depending on at which surface within the eye this comparison occurs.

In a preferred embodiment, only the ultimate step (in particular step 6b) is omitted, thus the propagation from the AP to the retina. After the refraction at the posterior lens surface, the incident wavefront is thus simulated only up to the AP (thus calculation of $S_{AP}$ according to the aforementioned step 6a), and there is compared with a reference wavefront $R_{AP}$. This is characterized in that, given the propagation to the retina, it yields a point image there. According to the above statement, the vergence matrix of this wavefront is $$R_{AP} = D_{AP} = D_{LR}^{(b)} = \frac{1}{\tau_{LR}^{(b)}}1 = \frac{1}{\tau_{LR} - \tau_{LR}^{(a)}}1 = \frac{1}{1/D_{IR} - d_{IR}^{(a)}/n_{LR}}1$$

with the $D_{LR}$ determined from Equation (2) or (3), as well as the negative (accommodation-dependent) value $d_{LR}^{(a)} < 0$ whose absolute magnitude describes the distance between the posterior lens surface and the AP.

In a furthermore preferred embodiment, the penultimate step is moreover omitted, overall thus the propagation from the posterior lens surface to the retina. The incident wavefront is thus only simulated up to after the refraction at the posterior lens surface (thus calculation of $S'_{L2}$ according to the aforementioned step 5), and there is compared with a reference wavefront $R'_{L2}$. This is characterized in that, given the propagation to the retina, it yields a point image there. According to the above statement, the vergence matrix of this wavefront is $$R'_{L2}=D'_{L2}=D_{LR}\cdot 1$$

with the $D_{LR}$ determined from Equation (2) or (3).

A further simplification results if the comparison is placed before the refraction by the posterior lens surface. In this instance, the incident wavefront is simulated, thus calculated, only up to $S_{L2}$ according to the above step 4. For this purpose, analogous to $S'_{L2}$, a reference wavefront $R_{L2}$ is defined that, after the refraction at the posterior lens surface and the propagation to the retina, yields a point image there. This is determined as $$R_{L2}=R'_{L2}-L_2=D_{LR}\cdot 1-L_2$$

with the $D_{LR}$ determined from Equation (2) or (3), and the $L_2$ known from the literature or from measurements.

In the event of a rotationally symmetrical posterior lens surface, this simplifies to $$R_{L2}=(D_{LR}-L_{2,xx})\cdot 1$$

In particular insofar as the lens thickness is likewise learned from the literature, in a further preferred embodiment it is suggested as a next simplification step to omit the propagation through the lens and to execute the comparison after the refraction through the anterior lens surface. In a continuation of the above statement, for this purpose a reference wavefront $R'_{L1}$ is preferably used that is created from $R_{L2}$ via backward propagation by the lens thickness, and possesses the following vergence matrix:

$$R'_{L1}=R_{L2}/(1+\tau_L R_{L2})$$

with the $D_{LR}$ determined from Equation (2) or (3) and the $\tau_L=d_L/n_L$, known from the literature or from measurements, as well as the vergence matrix $R_{L2}$ determined from Equation (6) or (7).

In the event of a rotationally symmetrical posterior lens surface, this simplifies to $$R'_{L1} = \frac{D_{LR} - L_{2,xx}}{1 + \tau_L \cdot (D_{LR} - L_{2,xx})} \cdot 1$$

As in the above models, it also applies here that, even if the consideration occurs before the last steps and—depending on notation—the variable $D_{LR}$ does not explicitly occur, this variable is nevertheless at least implicitly incurred together with $d_L$ and $L_2$, since they together control the distribution of the effect $L_1$ in the anterior lens surface.

Yet another simplification results if the comparison is placed before the refraction by the anterior lens surface. In this instance, the incident wavefront needs to be simplified only up to $S_{L1}$ according to step 2. For this purpose, analogous to $R'_{L1}$, a reference wavefront $R_{L1}$ is defined that converges at a point on the retina after the refraction at the anterior lens surface and the additional steps. This may either be calculated via the refraction of $R'_{L1}$ at $L_1$, or be determined directly from the refraction of the measured wavefront $S_M$ at the cornea C and a subsequent propagation by $d_{CL}$. In both instances, $$R_{L1} = \frac{S_M + C}{1 - \tau_{CL} \cdot (S_M + C)}$$

is obtained. The variables $D_{LR}$, $d_L$ and $L_2$ now no longer enter into it; it is thus sufficient to know $S_M$, C and $d_{CL}$.

An embodiment in which the comparison is implemented after the refraction at the cornea is linked with relatively low computation cost. In this instance, only $S_M$ and C are still considered:

$$R'_C=S_M+C$$

An additional, very efficient possibility is the positioning of the evaluation surface at the exit pupil of the model eye. This is preferably situated before the posterior lens surface.

Additional Aspects

Insofar as is not explicitly noted otherwise, aspects that are relevant to both the first and the second approach of the invention are described in the following paragraphs:

In particular, in the following commercially available devices are cited in summary, again by way of example, with which devices parameter measurements that are necessary or preferred for the invention may be implemented. All devices listed here are, for example, also described in M. Kaschke et al., "Optical Devices in Ophthalmology and Optometry", Wiley-VCH (2014):

Shape of the anterior corneal surface: The shape of the anterior corneal surface may be determined with keratographs (for example Placido-Disk Keratograph ATLAS 9000 from Zeiss, Small-Target Keratograph E300 from Medmont, and Placido Disk unit of the Galilei G2 from Ziemer). In the instances in which only the curvatures are determined and used, the use of keratometers is also possible (for example manual Helmholtz-Littmann keratometer from Zeiss, manual Javal-Schiötz keratometer from Haag-Streit, and automatic electro-optical keratometry unit of the IOL Master from Zeiss).

Shape of the anterior lens surface and posterior lens surface: The shape of the lens surfaces may be measured in a section or three-dimensionally with Scheimpflug cameras (for example Pantacam by Oculus, SL-45 by Topcon, and Galilei G2 by Ziemer), and OCTs (for example IOL Master of 500 by Zeiss, SL-OCT by Heidelberg, and Visante OCT by Zeiss).

Distance between the described surfaces: Distances between the three cited surfaces may be measured both with some of the aforementioned Scheimpflug cameras and OCTs, and with the Lenstar LS900 from Haag-Streit. Some of these devices might also, in fact, be used in order to measure the distance between these surfaces and the retina. However, such measurements are often very costly, and may be directly avoided within the scope of the present invention. For this purpose, refer for example to R. B. Rabbetts, "Bennett & Rabbetts' Clinical Visual Optics", Butterworth Heinemann Elsevier Health Sciences (2007).

Refraction indices of the participating media: A citation of devices with which the refraction indices of the participating may be measured may be omitted here, since these values are preferably taken from the literature. For this purpose, refer for example to R. B. Rabbetts, "Bennett & Rabbetts' Clinical Visual Optics", Butterworth Heinemann Elsevier Health Sciences (2007).

Higher-order or lower-order aberrations of the eye: aberrations of the eye may be measured with aberrometers (for example iProfiler from Zeiss and KR-1W from Topcon based on Schack-Hartmann sensors, as well as OPD-Scan 111 from Nidek based on dynamic skiascopy). Given a consideration of lower-order aberrations, the use of autorefractometers (for example RM-8900 from Topcon and KW-2000 from Kowa) is sufficient.

REFERENCE LIST 10 principal ray
12 eye
14 first surface of the spectacles lens (anterior surface)
16 second surface of the spectacles lens (posterior surface)
18 anterior corneal surface
20 eye lens

The invention claimed is:

1. A computer-implemented method for determining personalized parameters of at least one eye of a spectacles wearer, the method comprising:
   providing personalized refraction data of the at least one eye of the spectacles wearer; and
   establishing a personalized eye model in which at least:
      a shape of an anterior corneal surface of a model eye;
      a cornea to eye-lens distance;
      parameters of the eye-lens of the model eye; and
      an eye-lens to retina distance, are established degrees of freedom, which are established using (i) personalized measured values for the eye of the spectacles wearer, (ii) standard values, or (iii) the provided personalized refraction data, wherein the personalized eye model is established at least partly based on the provided personalized refraction data such that the model eye has the provided personalized refraction data, and
   wherein at least the eye-lens to retina distance is established via calculation based on the provided personalized refraction data and one or more of the established degrees of freedom of the personalized eye model other than the eye-lens to retina distance.

2. The method according to claim 1, wherein the establishing the shape of the anterior corneal surface of the eye takes place using personalized measurements at least in part along the principal section of the cornea of the at least one eye.

3. The method according to claim 1, wherein the establishing the shape of the anterior corneal surface of the eye takes place using personalized measurements of the corneal topography of the at least one eye.

4. The method according to claim 1, wherein the establishing the cornea to eye-lens distance takes place using personalized measured values for the cornea to eye-lens distance.

5. The method according to claim 1, wherein the establishing the parameters of the eye-lens of the model eye comprises an establishment of the following parameters:
   shape of the anterior eye-lens surface;
   eye-lens thickness; and
   shape of the posterior eye-lens surface.

6. The method according to claim 5, wherein the establishing the eye-lens thickness and of the shape of the posterior eye-lens surface takes place using predetermined standard values, and the establishment of the shape of the anterior eye-lens surface comprises:
   providing standard values for a mean curvature of the anterior eye-lens surface; and
   calculating the shape of the anterior eye-lens surface at least partially based on the provided personalized refraction data.

7. The method according to claim 5, wherein the establishing the shape of the anterior eye-lens surface comprises:
   providing a personalized measured value of a curvature in a normal section of the anterior eye-lens surface.

8. The method according to claim 7, wherein the establishing the eye-lens thickness and of the shape of the posterior eye-lens surface takes place using standard values, and the establishment of the anterior eye-lens surface comprises:
   providing a personalized measured value of a curvature in a normal section of the anterior eye-lens surface; and
   calculating the shape of the anterior eye-lens surface at least partially based on the provided personalized refraction data.

9. The method according to claim 1, wherein the establishing the parameters of the eye-lens of the model eye includes establishing an optical effect of the eye-lens.

10. The method according to claim 1, further comprising:
    displaying the calculated eye-lens to retina distance.

11. The method according to claim 1, further comprising:
    determining an eye length of the model eye, at least partially based on the calculated eye-lens to retina distance; and
    displaying the determined eye length.

12. A computer-implemented method, comprising:
    a method for determining personalized parameters of the at least one eye of the spectacles wearer according to claim 1;
    predetermining a shape of a first surface and a shape of second surface for the spectacles lens to be calculated or optimized;
    determining the path of a principal ray through at least one visual point (i) of at least one surface of the spectacles lens into the model eye, which surface is to be calculated or optimized;
    evaluating an aberration of a wavefront at an evaluation surface, said wavefront resulting along the primary ray from a spherical wavefront striking the first surface of the spectacles lens, in comparison to a wavefront converging at a point on the retina of the personalized eye model; and
    iteratively varying the at least one surface to be calculated or optimized, until the evaluated aberration corresponds to a predetermined target aberration.

13. The method according to claim 12, wherein the evaluation surface is situated between the eye-lens and the retina of the model eye.

14. The method according to claim 12, wherein the evaluation surface is situated at the exit pupil of the model eye.

15. A system for determining personalized parameters of at least one eye of a spectacles wearer, comprising:
    a data interface configured to provide personalized refraction data of the at least one eye of the spectacles wearer; and
    a modeler configured to establish a personalized eye model which is established on at least:
      a shape of an anterior corneal surface of a model eye;
      a cornea to eye-lens distance;

parameters of the eye-lens of the model eye; and
an eye-lens to retina distance, are established degrees of freedom, which are established using (i) personalized measured values for the eye of the spectacles wearer, (ii) standard values, or (iii) the provided personalized refraction data,
wherein the personalized eye model is established at least partly based on the provided personalized refraction data such that the model eye has the provided personalized refraction data, and
wherein at least the eye-lens to retina distance is established via calculation based on the provided personalized refraction data and one or more of the established degrees of freedom of the personalized eye model other than the eye-lens to retina distance.

16. The system according to claim 15, wherein the modeler is configured to determine an eye length of the model eye at least partially based on the calculated eye-lens to retina distance.

17. The system according to claim 16, further comprising:
a display configured to display the calculated eye-lens to retina distance or the determined eye length.

18. The system according to claim 15, wherein the personalized refraction data is measured by an aberrometer or the shape of the anterior corneal surface is measured by a topograph.

19. The system according to claim 15, further comprising:
a surface model database configured to predetermine a shape of a first surface and a shape of a second surface for the spectacles lens to be calculated or optimized;
a principal ray determiner configured to determine the path of a principal ray through at least one visual point (i) of at least one surface of the spectacles lens into the model eye, which surface is to be calculated or optimized;
an evaluator configured to evaluate an aberration of a wavefront at an evaluation surface, said wavefront resulting along the principal ray from a spherical wavefront striking the first surface of the spectacles lens, in comparison to a wavefront converging at a point on the retina of the personalized eye model; and
an optimizer configured to iteratively vary the at least one surface of the spectacles lens, said surface to be calculated or optimized, until the evaluated aberration corresponds to a predetermined target aberration.

20. A non-transitory computer program product having program code that is designed to implement a method for determining personalized parameters of at least one eye of a spectacles wearer according to claim 1, when loaded and executed on a computer.

21. A method for producing a spectacles lens, comprising:
calculating or optimizing a spectacles lens according to the method of claim 12; and
manufacturing the spectacles lens so calculated or optimized.

22. A system for producing a spectacles lens, comprising:
a calculator or optimizer configured to calculate or optimize a spectacles lens according to the method of claim 12; and
a machine configured to machine the spectacles lens according to the result of the calculation or optimization.

* * * * *